(12) United States Patent
Doles et al.

(10) Patent No.: US 12,201,536 B2
(45) Date of Patent: Jan. 21, 2025

(54) SYSTEMS AND METHODS FOR RESIDUAL LIMBS OF AMPUTEES

(71) Applicant: JSG IP Ventures, LLC, Greenwood Village, CO (US)

(72) Inventors: Jordan T. Doles, Fort Collins, CO (US); Michael Young, Greenwood Village, CO (US); Paul Goudreau, Edina, MN (US); Troy Winsand, Maple Grove, MN (US); Mark Hatcher, Hopkins, MN (US)

(73) Assignee: JSG IP VENTURES, LLC, Greenwood Village, CO (US)

( * ) Notice: Subject to any disclaimer, the term of this patent is extended or adjusted under 35 U.S.C. 154(b) by 0 days.

(21) Appl. No.: 18/738,539

(22) Filed: Jun. 10, 2024

(65) Prior Publication Data

US 2024/0325172 A1 Oct. 3, 2024

Related U.S. Application Data

(60) Continuation of application No. 18/629,778, filed on Apr. 8, 2024, which is a continuation-in-part of (Continued)

(51) Int. Cl.
*A61N 1/36* (2006.01)
*A61B 5/00* (2006.01)
(Continued)

(52) U.S. Cl.
CPC .............. *A61F 2/50* (2013.01); *A61B 5/377* (2021.01); *A61B 5/6811* (2013.01); *A61F 2/72* (2013.01);
(Continued)

(58) Field of Classification Search
CPC ..... A61N 1/0456; A61N 1/361; A61F 2/7812; A61F 2002/608; A61F 2002/6827
See application file for complete search history.

(56) References Cited

U.S. PATENT DOCUMENTS 8,945,236 B2 2/2015 Leiniger et al.
9,358,138 B2 6/2016 Kelley et al.
(Continued)

FOREIGN PATENT DOCUMENTS

DE 102015009828 A1 2/2017
DE 102021125702 A1 4/2022
(Continued)

OTHER PUBLICATIONS

"International Search Report and Written Opinion of the International Searching Authority," issued in connection with Int'l Appl. No. PCT/US2024/023642, dated Jul. 18, 2024 (14 pages).
(Continued)

*Primary Examiner* — Bruce E Snow
(74) *Attorney, Agent, or Firm* — Holland & Hart LLP

(57) ABSTRACT

Various aspects of this disclosure relate to a prosthetic cover comprising an array of sensors, which transmit signals to an array of electrodes in a liner that fits over a residual limb of an amputee. Different interactions with the prosthetic cover cause different activation of the electrodes to transmit electrical current through different areas of the residual limb and modulate neurons differently within the residual limb. Various aspects of this disclosure also relate to a prosthetic liner with a substrate that includes electrodes for transcutaneous electrical nerve stimulation and/or electronic muscle stimulation for a residual limb.

25 Claims, 11 Drawing Sheets

Related U.S. Application Data application No. 18/510,337, filed on Nov. 15, 2023, now Pat. No. 11,986,402, which is a division of application No. 18/296,970, filed on Apr. 6, 2023, now Pat. No. 11,833,064.

(60) Provisional application No. 63/348,967, filed on Jun. 3, 2022.

(51) Int. Cl.
| | | |
|---|---|---|
| *A61B 5/377* | (2021.01) | |
| *A61F 2/50* | (2006.01) | |
| *A61F 2/72* | (2006.01) | |
| *A61F 2/78* | (2006.01) | |
| *A61N 1/04* | (2006.01) | |
| *A61F 2/60* | (2006.01) | |
| *A61F 2/68* | (2006.01) | |
| *A61F 2/70* | (2006.01) | |

(52) U.S. Cl.
CPC ......... *A61N 1/0456* (2013.01); *A61N 1/3606* (2013.01); *A61N 1/361* (2013.01); *A61F 2002/608* (2013.01); *A61F 2/68* (2013.01); *A61F 2002/6827* (2013.01); *A61F 2/70* (2013.01); *A61F 2/7812* (2013.01); *A61N 1/36071* (2013.01)

(56) References Cited

U.S. PATENT DOCUMENTS

| | | |
|---|---|---|
| 9,615,944 B2 | 4/2017 | Will et al. |
| 11,577,045 B2 | 2/2023 | Perry et al. |
| 11,833,064 B1 | 12/2023 | Doles |
| 11,986,402 B2 | 5/2024 | Doles |
| 2009/0216339 A1 | 8/2009 | Hanson et al. |
| 2012/0101595 A1 | 4/2012 | Jung et al. |
| 2012/0296445 A1* | 11/2012 | Leiniger ............... A61F 2/7812 623/33 |
| 2014/0188251 A1 | 7/2014 | Mosler et al. |
| 2015/0142129 A1 | 5/2015 | Kirn |
| 2016/0263345 A1 | 9/2016 | Shuster et al. |
| 2016/0331561 A1 | 11/2016 | Raspopovic et al. |
| 2017/0311827 A1 | 11/2017 | Choi et al. |
| 2018/0296822 A1* | 10/2018 | Schroeder ............. A61L 31/126 |
| 2019/0254845 A1 | 8/2019 | Wernke et al. |
| 2021/0186719 A1* | 6/2021 | Laghi ................... A61F 2/7812 |
| 2022/0031480 A1 | 2/2022 | Bause et al. |
| 2023/0293318 A1 | 9/2023 | Kaltenborn et al. |

FOREIGN PATENT DOCUMENTS

| | | |
|---|---|---|
| EP | 2962726 B1 | 11/2020 |
| WO | 2019/025838 A1 | 2/2019 |

OTHER PUBLICATIONS

Culp, C. J., "Current Understanding of Phantom Pain and its Treatment", Pain Physician, 2022, vol. 25, pp. E941-E957.

* cited by examiner

SYSTEMS AND METHODS FOR RESIDUAL LIMBS OF AMPUTEES

CROSS-REFERENCE TO RELATED APPLICATIONS

This patent application is a continuation application of U.S. patent application Ser. No. 18/629,778, filed Apr. 8, 2024, which is a continuation-in-part application of U.S. patent application Ser. No. 18/510,337, filed Nov. 15, 2023, which is a continuation application of U.S. patent Ser. No. 18/296,970, filed Apr. 6, 2023, which claims priority to U.S. Provisional Patent Application No. 63/348,967, filed Jun. 3, 2022, all of which are incorporated by reference in their entirety.

BACKGROUND

Amputees frequently suffer from phantom limb syndrome, in which they experience sensations that they attribute to a missing limb. These sensations are generally undesirable, frequently painful, and, in some cases, debilitating.

Phantom limb syndrome may be treated by mirror therapy, in which a mirror provides a visual representation of a missing limb when placed between intact and missing limbs. As patients move their intact limbs, two limbs appear to move concurrently. This provides patients with a visual representation of their missing limbs, which affects the way they feel their missing limbs following repeated therapy. Clinical research on mirror therapy has not, however, demonstrated a statistically significant effect on reducing pain.

Other non-pharmacological interventions to reduce symptoms of phantom limb syndrome remain desirable.

SUMMARY

Various aspects of this disclosure relate to the finding that neural feedback from interactions with a prosthesis and/or a prosthesis liner can help alleviate symptoms of phantom limb syndrome.

Some embodiments relate to a prosthetic cover comprising an array of sensors, which transmit signals to an array of electrodes in a liner that fits over a residual limb of an amputee. Different interactions with the prosthetic cover cause different activation of the electrodes to transmit electrical current through different areas of the residual limb and modulate neurons differently within the residual limb. An amputee can therefore interact with a prosthetic by touching the cover, viewing the interaction, and modulating different neurons in response to touch. Without limiting this specification or any patent claim that matures from this disclosure, simultaneous sensory feedback from touch, vision, and electrical current favorably induces neuroplasticity in the somatosensory cortex of the brain of an amputee to create a new topographic map for the prosthetic through repeated interaction, which reduces symptoms of phantom limb syndrome. Without limiting this specification or any patent claim that matures from this disclosure, the new topographic map allows amputees to associate specific symptoms of phantom limb syndrome with specific interactions with the prosthetic cover, which allows amputees to treat the specific symptoms as they arise via the specific interactions.

Various aspects of this disclosure include systems and methods that include a prosthetic liner configured for electrical communication (e.g., electrical stimulation) with a residual limb of an amputee. In some embodiments, the system is a system for modulating nerve activation or muscle stimulation in the residual limb. In some specific embodiments, the system is a system for stimulating Aβ nerve fibers in the residual limb.

In some embodiments, the system comprises a prosthetic liner, or a substrate (or insert) incorporated into a prosthetic liner, that houses electrodes. In some embodiments, the prosthetic liner may be molded (e.g., overmolded, insert molded) onto the substrate.

The substrate may include electrodes that are embedded or otherwise incorporated into the substrate or the liner. In some specific embodiments, the substrate is a polymer (e.g., silicone).

In some embodiments, the substrate may include a conductor. In some embodiments, the conductor may be a plurality of wires that are at least partially incorporated into the substrate. In some embodiments, the conductor may be a conductive material (e.g., an elastomer).

In some embodiments, systems for modulating nerve activation in a residual limb of an amputee comprise a prosthetic liner, including: a polymer substrate that comprises electrodes, the prosthetic liner configured to receive the residual limb such that each electrode in the polymer substrate is in electrical communication with the residual limb and the electrodes are configured such that transmitting electrical current through the residual limb, with an electrode controller in electrical communication with each electrode, stimulates Aβ nerve fibers in the residual limb.

In some embodiments, the amputee presents with phantom limb syndrome, and the system is configured such that the electrical current treats one or more symptoms of the phantom limb syndrome.

In some embodiments, the electrodes have an electrode three-dimensional configuration relative to the liner. The three-dimensional configuration is any configuration for two or more electrodes to form a ring around a residual limb. In some embodiments, the plurality of electrodes are configured in a ring that includes at least two electrodes spaced in the liner to transmit electrical current in different locations on the residual limb. In some embodiments, the plurality of electrodes include electrodes A, B, C, and D. In some embodiments, the controller transmits electricity from electrode A through the residual limb to both electrode B and electrode D. In some embodiments, the plurality of electrodes include an anterior-proximal electrode, an anterior-distal electrode, a lateral-proximal electrode, and a lateral-distal electrode. In some embodiments, the plurality of electrodes include anterior-lateral-proximal electrode, a posterior-lateral-proximal electrode, a posterior-medial-proximal electrode, and an anterior-medial-proximal electrode. In some embodiments, configurations do not surround a residual limb. In some embodiments, the electrical current is pulsed electrical current. The pulsed electrical current may have a pulse frequency at least 20 and up to 180 pulses per second, a pulse width of up to 100 microseconds, and an amplitude of up to 100 milliamps.

In some embodiments, the systems comprises a secondary controller in wireless communication with the electrodes configured to cause one or more electrodes to transmit electrical current to the residual limb. The secondary controller may be a mobile computing device, in wireless communication with the electrodes, and the wireless communication is mediated by one or both of a Bluetooth or Wi-Fi connection between the mobile computing device and the electrodes.

In some embodiments, the methods include modulating nerve activation in a residual limb of an amputee. The methods may include providing a system that comprises a prosthetic liner, the prosthetic liner including a polymer substrate with a plurality of electrodes in electrical communication with an electrode controller and configured to attach to the residual limb such that the plurality of electrodes is in electrical communication with the residual limb; transmitting, with the electrode controller in electrical communication with each electrode, electrical current through the residual limb; and stimulating Aβ nerve fibers in the residual limb responsive to transmitting electrical current with the plurality of electrodes.

In some embodiments, the methods include stimulating muscles in the residual limb responsive to transmitting electrical current with the plurality of electrodes. The amputee may present with phantom limb syndrome; and the methods further treat one or more symptoms of the phantom limb syndrome with transmission of the electrical current.

In some embodiments, the methods include transmitting pulsed electrical current with a pulse frequency at least 20 and up to 180 pulses per second, a pulse width of up to 100 microseconds, and an amplitude of up to 100 milliamps.

In some embodiments, the methods include transmitting, with a secondary controller in wireless communication with the electrode controller, electrical current to the residual limb.

In some embodiments, the systems include modulating nerve activation in a residual limb of an amputee with a user interface configured to receive an input from the amputee and display an output; a processor, memory in electronic communication with the processor; and instructions stored in the memory and executable by the processor to cause the apparatus to: transmit, with an electrode controller in electrical communication with an electrode in a prosthetic liner substrate, electrical current through the residual limb; and stimulate Aβ nerve fibers in the residual limb responsive to transmitting electrical current with the electrode.

In some embodiments, the disclosed technology includes non-transitory computer-readable medium comprising instructions to cause a processor to: transmit with an electrode controller in electrical communication with an electrode in a prosthetic liner substrate, electrical current through a residual limb of an amputee; and stimulate Aβ nerve fibers in the residual limb responsive to transmitting electrical current with the electrode. The processor may be further configured to detect physiological parameters with at least one sensor; measures physiological data from the physiological parameters; store the measured physiological data; processes the measured physiological data; and provide outputs to a user or other computing device responsive to processing the measured physiological data.

Various other aspects of the inventions of this disclosure will become apparent upon review of the following detailed description and claims. The scope of this disclosure shall not be limited by the foregoing summary and background. The scope of each patent claim that matures from this disclosure shall not be limited by the foregoing summary and background or by the following detailed description, and the scope of each patent claim that matures from this disclosure shall instead be limited solely by the explicit language of the claim in the context of its claim dependency.

DETAILED DESCRIPTION

Figure 1:
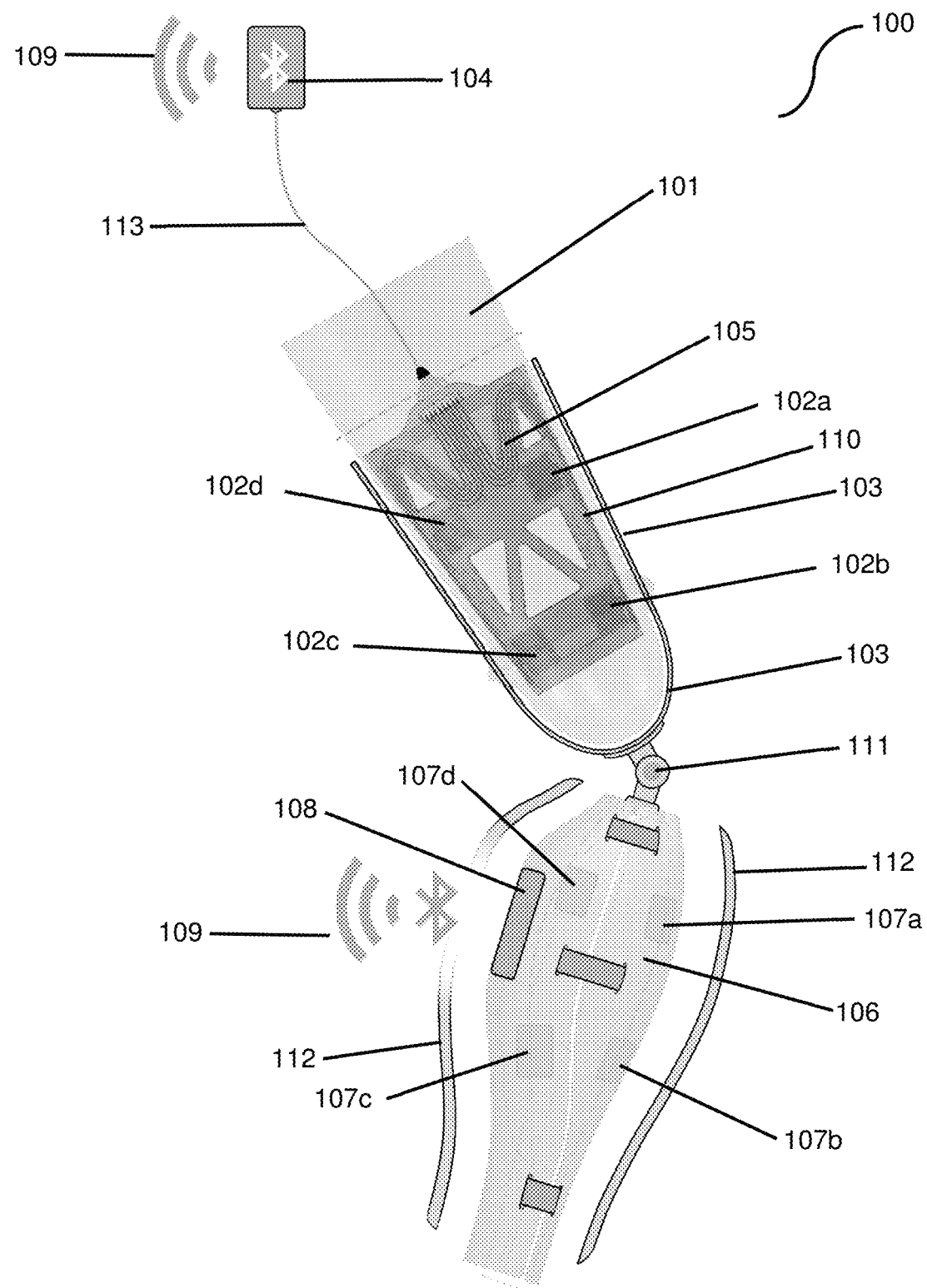
FIG. 1 depicts a system comprising a liner that comprises an array of embedded electrodes and a prosthetic cover that comprises an array of sensors.

The disclosed technology includes systems and methods to treat phantom limb syndrome by treating symptoms of phantom limb pain and increasing an amputee's proprioceptive senses of a prosthetic limb.

Following amputation of a limb, an amputee may report perception of a feeling of the missing limb, known as phantom limb sensation (PLS). In some cases, the feeling can be pain or discomfort in the missing limb, known as phantom limb pain (PLP). In extreme cases, PLP presents a debilitating condition.

Various aspects of this disclosure relate to a prosthetic cover comprising an array of sensors, which transmit signals to an array of electrodes in a liner that fits over a residual limb of an amputee. Different interactions with the prosthetic cover cause different activation of the electrodes to transmit electrical current through different areas of the residual limb and modulate neurons differently within the residual limb. As a result of the interactions with the prosthetic cover, electrical stimulation to underlying nerve fibers provide an amputee the ability to feel a stimulus. The stimuli, alone or in combination with other PLP treatment applications (e.g., artificial visualization, such as mirror therapy), can evoke a somatic sensation. As a result, the amputee may perceive the missing limb is intact and/or functional, which can decrease or resolve PLP.

In some embodiments, interactions with the prosthetic cover are any interactions, events, or modalities sensed by sensors that cause activation of the electrodes. In some embodiments, a modality is a touch modality, such as touch, force, pressure, flutter, or vibration.

Various aspects of this disclosure relate to a system for use by an amputee. In some embodiments, the system is for modulating nerve activation in a residual limb of an amputee.

In some embodiments, the system comprises a prosthetic liner or a substrate in a liner with electrodes. The substrate may be incorporated into a liner. In some specific embodiments, the system comprises a prosthetic liner or substrate that comprises an array of electrodes. In some very specific embodiments, the system comprises a liner or substrate that comprises an embedded array of electrodes. A liner or substrate generally comprises or consists of a non-conductive polymer such as silicone.

In some embodiments, the system comprises an array of electrodes. In some specific embodiments, the system comprises an array of electrodes that are embedded in a liner. An array of electrodes may be embedded, for example, in a silicone liner. Any medical-grade electrode capable of conducting at least 30 milliamps of pulsed electrical current is generally suitable for use with the systems and methods described herein. In some specific embodiments, an electrode is suitable for electronic muscle stimulation. In some specific embodiments, an electrode is suitable for transcutaneous electrical nerve stimulation. In some specific embodiments, electrodes are suitable for both electronic muscle stimulation and transcutaneous electrical nerve stimulation. In some very specific embodiments, an electrode is a carbon rubber electrode.

The electrodes of this disclosure are generally suitable for continuous, long-term contact with human skin, which contact is optionally mediated by a conductive gel. In some embodiments, continuous, long-term contact refers to at least two hours of continuous contact. In some specific embodiments, continuous, long-term contact refers to at least twelve hours of continuous contact. In some very specific embodiments, continuous, long-term contact refers to at least 48 hours of continuous contact.

In some embodiments, the liner or the substrate in a liner is a single, unified structure. In some specific embodiments, the liner or the substrate in a liner is a single, unified structure in which the array of electrodes is embedded. In some very specific embodiments, the liner or the substrate in a liner is a single, unified structure in which the array of electrodes and wires are embedded, wherein each electrode of the array of electrodes is connected to at least one wire such that the wires can mediate electrical communication between the array of electrodes and an electrode controller. The electrodes may comprise, for example, 2-millimeter pin connectors to create electrical communication between the electrodes and the wires. The liner may be formed, for example, by providing a substrate that comprises the electrodes and wires, inserting the substrate into a mold, and pouring liquid silicone into the mold such that the electrodes and wires become embedded in the silicone.

The liner or the substrate in a liner is generally configured to receive a residual limb of an amputee. In some specific embodiments, the liner or the substrate in a liner is configured to receive the residual limb such that each electrode of the array of electrodes is in electrical communication with the residual limb. A conductive gel may be applied, for example, between the electrodes of an array of electrodes and a residual limb to facilitate electrical communication between the electrodes and the residual limb.

This disclosure and the claims shall not be construed to suggest that a system of the disclosure or claims includes an amputee, a residual limb, nerve fiber, or the like unless explicit language states that the system comprises the amputee, residual limb, nerve fiber, or the like, and, if any explicit language states that the system comprises the amputee, residual limb, nerve fiber, or the like, then that explicit language shall be limited to its immediate context and shall not be used to construe other sections of this disclosure that lack the explicit language or to construe any patent claim that both matures from this disclosure and lacks the explicit language.

In some embodiments, each electrode of the array of electrodes is paired with at least two other electrodes of the array of electrodes such that, when the array of electrodes is in electrical communication with the residual limb, then each electrode can (1) transmit electrical current through the residual limb both to a first negative electrode with which the electrode is paired and, independently, to a second negative electrode with which the electrode is paired and/or (2) receive electrical current through the residual limb from both a first positive electrode with which the electrode is paired and, independently, from a second positive electrode with which the electrode is paired. In such embodiments, each electrode of the array of electrodes can transfer electrical current through and/or receive electrical current from at least two other electrodes to provide different paths of electrical current through the residual limb, for example, in response to different sensors and/or to differentially modulate nerve fibers in the residual limb.

In some embodiments, the system is configured such that when (1) two or more electrodes are activated and (2) the two or more electrodes are in electrical communication with the residual limb, then one electrode of the activated two or more electrodes transmits electrical current though the residual limb and another electrode of the activated two or more electrodes receives the electrical current that is transmitted through the residual limb. In some specific embodiments, the system is configured such that when (1) two electrodes are activated and (2) the two electrodes are in electrical communication with the residual limb, then one electrode of the activated two electrodes transmits electrical current though the residual limb and the other electrode of the activated two electrodes receives the electrical current that is transmitted through the residual limb. An electrode is activated when the electrode is transmitting or receiving electrical current.

In some embodiments, the system comprises an electrode controller in electrical communication with each electrode of the array of electrodes.

In some embodiments, the electrode controller is configured to control whether each electrode that can transmit electrical current transmits the electrical current to a negative electrode. In some embodiments, the electrode controller is configured to control whether each electrode that can receive electrical current receives the electrical current from a positive electrode. In some specific embodiments, the electrode controller is configured to control both whether each electrode that can transmit electrical current transmits the electrical current to a negative electrode and whether each electrode that can receive electrical current receives the electrical current from a positive electrode. An electrode controller can therefore control which electrodes of the array of electrodes transmit and receive electrical current, for example, in response to different sensors and/or to transmit electrical current through different regions of the residual limb.

In some embodiments, the electrode controller is configured to control whether each electrode that can transmit electrical current transmits the electrical current through the residual limb to one or both of a first negative electrode and a second negative electrode. In some embodiments, the electrode controller is configured to control whether each electrode that can receive electrical current receives the electrical current from one or both of a first positive electrode and a second positive electrode. In some specific embodiments, the electrode controller is configured to control both whether each electrode that can transmit electrical current transmits the electrical current through the residual limb to one or both of a first negative electrode and a second negative electrode and whether each electrode that can receive electrical current receives the electrical current from one or both of a first positive electrode and a second positive electrode.

In some embodiments, the electrode controller controls the electrical current transmitted or received by each electrode of the array of electrodes.

In some embodiments, the system is configured such that transmitting and receiving electrical current through the residual limb modulates nerve fibers in the residual limb. In some specific embodiments, the system is configured such that transmitting and receiving electrical current through the residual limb stimulates nerve fibers in the residual limb. In some very specific embodiments, the system is configured such that transmitting and receiving electrical current through the residual limb stimulates myelinated Aβ nerve fibers in the residual limb. In some very specific embodiments, the system is configured such that transmitting and receiving electrical current through the residual limb modulates the activation of myelinated Aδ nerve fibers in the residual limb. In some very specific embodiments, the system is configured such that transmitting and receiving electrical current through the residual limb modulates the activation of unmyelinated C nerve fibers in the residual limb.

In some embodiments, the array of electrodes is configured such that transmitting and receiving electrical current through the residual limb modulates nerve fibers in the residual limb. In some specific embodiments, the array of electrodes is configured such that transmitting and receiving electrical current through the residual limb stimulates nerve fibers in the residual limb. In some very specific embodiments, the array of electrodes is configured such that transmitting and receiving electrical current through the residual limb stimulates myelinated Aβ nerve fibers in the residual limb. In some very specific embodiments, the array of electrodes is configured such that transmitting and receiving electrical current through the residual limb modulates the activation of myelinated Aδ nerve fibers in the residual limb. In some very specific embodiments, the array of electrodes is configured such that transmitting and receiving electrical current through the residual limb modulates the activation of unmyelinated C nerve fibers in the residual limb.

In some embodiments, each electrode of the array of electrodes is configured such that transmitting and receiving electrical current through the residual limb modulates nerve fibers in the residual limb. In some specific embodiments, each electrode of the array of electrodes is configured such that transmitting and receiving electrical current through the residual limb stimulates nerve fibers in the residual limb. In some very specific embodiments, each electrode of the array of electrodes is configured such that transmitting and receiving electrical current through the residual limb stimulates myelinated Aβ nerve fibers in the residual limb. In some very specific embodiments, each electrode of the array of electrodes is configured such that transmitting and receiving electrical current through the residual limb modulates the activation of myelinated Aδ nerve fibers in the residual limb. In some very specific embodiments, each electrode of the array of electrodes is configured such that transmitting and receiving electrical current through the residual limb modulates the activation of unmyelinated C nerve fibers in the residual limb.

In some embodiments, the electrical current is pulsed electrical current.

In some embodiments, the pulsed electrical current has a pulse frequency of at least 2 and up to 200 pulses per second. In some specific embodiments, the pulsed electrical current has a pulse frequency of at least 20 and up to 180 pulses per second. In some very specific embodiments, the pulsed electrical current has a pulse frequency of at least 135 and up to 155 pulses per second.

In some embodiments, the pulsed electrical current has a pulse width of up to 400 microseconds. In some specific embodiments, the pulsed electrical current has a pulse width of up to 100 microseconds. In some very specific embodiments, the pulsed electrical current has a pulse width of up to 50 microseconds.

In some embodiments, the pulsed electrical current has an amplitude of up to 150 milliamps. In some specific embodiments, the pulsed electrical current has an amplitude of up to 100 milliamps. In some very specific embodiments, the pulsed electrical current has an amplitude of at least 10 and up to 30 milliamps.

In some embodiments, an array of electrodes comprises at least 4, 5, 6, 7, 8, 9, 10, 11, 12, 14, 16, 18, 20, 24, 28, 32, 64, 128, or 256 electrodes. In some specific embodiments, an array of electrodes comprises at least 8 and up to 512 electrodes. In some specific embodiments, an array of electrodes comprises 4, 5, 6, 7, 8, 9, 10, 11, 12, 14, 16, 18, 20, 24, 28, 32, 64, 128, 256, or 512 electrodes. In some very specific embodiments, an array of electrodes comprises 4, 5, 6, 7, 8, 9, 10, 11, 12, 14, 16, 18, 20, 24, 28, 32, 64, 128, 256, or 512 electrodes, and the system comprises a plurality of additional electrodes that are not included in the array of electrodes.

In some embodiments, the system comprises one or more electrodes that are not included in the array of electrodes. The unincluded one or more electrodes may be, for example, electrodes that are not used to transmit and/or receive electrical current to and/or from a residual limb or electrodes that a prospective infringer of one or more patent claims that mature from this disclosure might contemplate including in a system in an attempt to develop a legal theory of non-infringement.

In some embodiments, the system comprises a cover. In some specific embodiments, the system comprises a cover configured to receive a prosthesis. In some very specific embodiments, the system comprises a cover configured to receive a leg or arm prosthesis.

In some embodiments, the system lacks a prosthesis. This disclosure and the pendant claims shall not be construed to suggest that a system of the disclosure or pendant claims includes a prosthesis unless explicit language states that the system comprises the prosthesis, and, if any explicit language states that the system comprises the prosthesis, then that explicit language shall be limited to its immediate context and shall not be used to construe other sections of this disclosure that lack the explicit language or to construe any patent claim that both matures from this disclosure and lacks the explicit language.

In some embodiments, the system comprises a prosthesis.

In some embodiments, the cover is configured to overlay an outer surface of a prosthesis.

In some embodiments, the system comprises a polymer foam. In some specific embodiments, the system comprises polyurethane foam. In some very specific embodiments, the system comprises 2-part polyurethane expanding foam.

In some embodiments, the foam is configured to affix the cover to a prosthesis. In some specific embodiments, the foam is configured to fill void space between the cover and a prosthesis. In some very specific embodiments, the foam is configured to affix the cover to a prosthesis and to fill void space between the cover and the prosthesis.

In some embodiments, the foam contacts an inner surface of the cover. In some specific embodiments, the foam contacts an inner surface of the cover to affix the cover to a prosthesis. In some very specific embodiments, the foam contacts an inner surface of the cover to affix the cover to a prosthesis and to fill void space between the cover and the prosthesis.

In some embodiments, the system comprises a polymer foam, and the cover is affixed to the prosthesis with the polymer foam. In some specific embodiments, the system comprises polyurethane foam, and the cover is affixed to the prosthesis with the polyurethane foam. In some very specific embodiments, the system comprises 2-part polyurethane expanding foam, and the cover is affixed to the prosthesis with the 2-part polyurethane expanding foam. A cover may be affixed to a prosthesis, for example, by positioning the cover around the prosthesis and then inserting expanding foam between the cover and the prosthesis to fill void space between the cover and the prosthesis; the cover may thereby be affixed to different prostheses of different shapes and sizes.

In some embodiments, the foam (or components thereof) is provided in one or more containers. In some specific embodiments, the foam (or components thereof) is provided in one or more containers for use to affix the cover to a prosthesis. In some very specific embodiments, the foam (or components thereof) is provided in one or more containers for use to affix the cover to a prosthesis by inserting the foam (or components thereof) between the cover and the prosthesis to fill void space between the cover and the prosthesis.

In some embodiments, the system comprises one or more containers that contain an expandable foam. In some specific embodiments, the system comprises one or more containers that are bags that contain an expandable foam. An expandable foam may be provided, for example, in one or more containers that are bags, and the expandable foam may be expanded within the one or more bags while the one or more bags are positioned between a prosthesis and the cover to fill void space between the prosthesis and the cover and thereby affix the cover to the prosthesis. One or more bags can therefore be used, for example, to retain expandable foam within void space between a prosthesis and cover and/or to inhibit the expandable foam from entering void space within the prosthesis or cover and/or to inhibit the expandable foam from exiting the cover.

In some embodiments, the system comprises one or more straps to affix the cover to the prosthesis. Straps may be used, for example, to position the cover relative to a prosthesis prior to expanding foam within void space between the prosthesis and the cover.

In some embodiments, the cover comprises an array of sensors.

In some embodiments, each sensor of the array of sensors is configured to sense at least one modality (e.g., one or both of force and pressure). Each sensor may be, for example, a force sensing resistor.

In some embodiments, each sensor of the array of sensors comprises a resistor that is configured to sense at least one modality (e.g., one or both of force and pressure). The precise type of modality sensor is not limiting.

In some embodiments, the system is configured such that the amplitude of the electrical current transmitted and received by electrodes of the array of electrodes through the residual limb directly correlates with a modality (e.g., pressure or force) sensed by a sensor, for example, such that increased modality (e.g., increased pressure or increased force) correlates with increased amplitude.

In some embodiments, the array of electrodes is in communication with the array of sensors such that two or more electrodes are activated in response to sensing by one or more sensors. In some specific embodiments, the array of electrodes is in communication with the array of sensors such that two electrodes are activated in response to sensing by one sensor.

In some embodiments, each sensor corresponds to at least two electrodes. In some specific embodiments, each sensor corresponds to two electrodes.

In some embodiments, each electrode corresponds to at least one sensor. In some specific embodiments, each electrode corresponds to at least two sensors.

A sensor corresponds to an electrode if the sensor is in communication with the electrode such that the electrode will transmit or receive electrical current to or from the residual limb when both the sensor senses a modality (e.g., force or pressure) and the electrode is in electrical communication with the residual limb.

An electrode corresponds to a sensor if the sensor is in communication with the electrode such that the electrode will transmit or receive electrical current to or from the residual limb when both the sensor senses a modality (e.g., force or pressure) and the electrode is in electrical communication with the residual limb.

In some embodiments, the array of sensors has a sensor three-dimensional configuration relative to the cover.

In some embodiments, the array of sensors has a sensor three-dimensional configuration relative to an outer surface of a prosthesis when the cover is attached to the outer surface of the prosthesis.

In some embodiments, the array of electrodes has an electrode three-dimensional configuration relative to the liner.

In some embodiments, the array of electrodes has an electrode three-dimensional configuration relative to the residual limb when each of the electrodes is in electrical communication with the residual limb.

In some embodiments, each sensor has a sensor relative position in the sensor three-dimensional configuration relative to every other sensor of the array of sensors; each electrode has an electrode relative position in the electrode three-dimensional configuration relative to every other electrode of the array of electrodes; the system comprises sensor-electrode pairs that each consist of one or more sensors and two or more electrodes, which sensor(s) and electrodes correspond to each other; and the sensor relative position of each sensor of a sensor-electrode pair within the sensor three-dimensional configuration correlates with the electrode relative position of each electrode of the same sensor-electrode pair within the electrode three-dimensional configuration. In some specific embodiments, the system comprises sensor-electrode pairs that each comprise one sensor and two electrodes, which sensor and electrodes correspond to each other.

A sensor relative position correlates with an electrode relative position, for example, when (a) the sensors comprise an anterior-proximal sensor, an anterior-distal sensor, a lateral-proximal sensor, a lateral-distal sensor, a posterior-proximal sensor, a posterior-distal sensor, a medial-proximal sensor, and a medial-distal sensor; (b) the electrodes comprise an anterior-proximal electrode, an anterior-distal electrode, a lateral-proximal electrode, a lateral-distal electrode, a posterior-proximal electrode, a posterior-distal electrode, a medial-proximal electrode, and a medial-distal electrode; (c) the sensor-electrode pairs comprise each of an anterior-proximal pair that comprises the anterior-proximal sensor and the anterior-proximal electrode, an anterior-distal pair that comprises the anterior-distal sensor and the anterior-distal electrode, a lateral-proximal pair that comprises the lateral-proximal sensor and the lateral-proximal electrode, a lateral-distal pair that comprises the lateral-distal sensor and the lateral-distal electrode, a posterior-proximal pair that comprises the posterior-proximal sensor and the posterior-proximal electrode, a posterior-distal pair that comprises the posterior-distal sensor and the posterior-distal electrode, a medial-proximal pair that comprises the medial-proximal sensor and the medial-proximal electrode, and a medial-distal pair that comprises the medial-distal sensor and the medial-distal electrode; (d) the sensor relative position of the anterior-proximal sensor is (1) closer to the anterior-distal sensor than both the lateral-distal sensor and the medial-distal sensor, (2) closer to both the lateral-distal sensor and the medial-distal sensor than the posterior-distal sensor, (3) closer to both the lateral-proximal sensor and the medial-proximal sensor than the posterior-proximal sensor, and (4) closer to the posterior-proximal sensor than the posterior-distal sensor; (e) the electrode relative position of the anterior-proximal electrode is (1) closer to the anterior-distal electrode than both the lateral-distal electrode and the medial-distal electrode, (2) closer to both the lateral-distal electrode and the medial-distal electrode than the posterior-distal electrode, (3) closer to both the lateral-proximal electrode and the medial-proximal electrode than the posterior-proximal electrode, and (4) closer to the posterior-proximal electrode than the posterior-distal electrode; (f) the sensor relative position of the anterior-distal sensor is (1) closer to the anterior-proximal sensor than both the lateral-proximal sensor and the medial-proximal sensor, (2) closer to both the lateral-proximal sensor and the medial-proximal sensor than the posterior-proximal sensor, (3) closer to both the lateral-distal sensor and the medial-distal sensor than the posterior-distal sensor, and (4) closer to the posterior-distal sensor than the posterior-proximal sensor; (g) the electrode relative position of the anterior-distal electrode is (1) closer to the anterior-proximal electrode than both the lateral-proximal electrode and the medial-proximal electrode, (2) closer to both the lateral-proximal electrode and the medial-proximal electrode than the posterior-proximal electrode, (3) closer to both the lateral-distal electrode and the medial-distal electrode than the posterior-distal electrode, and (4) closer to the posterior-distal electrode than the posterior-proximal electrode; (h) the sensor relative position of the medial-proximal sensor is (1) closer to the medial-distal sensor than both the anterior-distal sensor and the posterior-distal sensor, (2) closer to both the anterior-distal sensor and the posterior-distal sensor than the lateral-distal sensor, (3) closer to both the anterior-proximal sensor and the posterior-proximal sensor than the lateral-proximal sensor, and (4) closer to the lateral-proximal sensor than the lateral-distal sensor; (i) the electrode relative position of the medial-proximal electrode is (1) closer to the medial-distal electrode than both the anterior-distal electrode and the posterior-distal electrode, (2) closer to both the anterior-distal electrode and the posterior-distal electrode than the lateral-distal electrode, (3) closer to both the anterior-proximal electrode and the posterior-proximal electrode than the lateral-proximal electrode, and (4) closer to the lateral-proximal electrode than the lateral-distal electrode; (j) the sensor relative position of the medial-distal sensor is (1) closer to the medial-proximal sensor than both the anterior-proximal sensor and the posterior-proximal sensor, (2) closer to both the anterior-proximal sensor and the posterior-proximal sensor than the lateral-proximal sensor, (3) closer to both the anterior-distal sensor and the posterior-distal sensor than the lateral-distal sensor, and (4) closer to the lateral-distal sensor than the lateral-proximal sensor; (k) the electrode relative position of the medial-distal electrode is (1) closer to the medial-proximal electrode than both the anterior-proximal electrode and the posterior-proximal electrode, (2) closer to both the anterior-proximal electrode and the posterior-proximal electrode than the lateral-proximal electrode, (3) closer to both the anterior-distal electrode and the posterior-distal electrode than the lateral-distal electrode, and (4) closer to the lateral-distal electrode than the lateral-proximal electrode; (l) the sensor relative position of the posterior-proximal sensor is (1) closer to the posterior-distal sensor than both the lateral-distal sensor and the medial-distal sensor, (2) closer to both the lateral-distal sensor and the medial-distal sensor than the anterior-distal sensor, (3) closer to both the lateral-proximal sensor and the medial-proximal sensor than the anterior-proximal sensor, and (4) closer to the anterior-proximal sensor than the anterior-distal sensor; (m) the electrode relative position of the posterior-proximal electrode is (1) closer to the posterior-distal electrode than both the lateral-distal electrode and the medial-distal electrode, (2) closer to both the lateral-distal electrode and the medial-distal electrode than the anterior-distal electrode, (3) closer to both the lateral-proximal electrode and the medial-proximal electrode than the anterior-proximal electrode, and (4) closer to the anterior-proximal electrode than the anterior-distal electrode; (n) the sensor relative position of the posterior-distal sensor is (1) closer to the posterior-proximal sensor than both the lateral-proximal sensor and the medial-proximal sensor, (2) closer to both the lateral-proximal sensor and the medial-proximal sensor than the anterior-proximal sensor, (3) closer to both the lateral-distal sensor and the medial-distal sensor than the anterior-distal sensor, and (4) closer to the anterior-distal sensor than the anterior-proximal sensor; (0) the electrode relative position of the posterior-distal electrode is (1) closer to the posterior-proximal electrode than both the lateral-proximal electrode and the medial-proximal electrode, (2) closer to both the lateral-proximal electrode and the medial-proximal electrode than the anterior-proximal electrode, (3) closer to both the lateral-distal electrode and the medial-distal electrode than the anterior-distal electrode, and (4) closer to the anterior-proximal electrode than the anterior-distal electrode; (p) the sensor relative position of the lateral-proximal sensor is (1) closer to the lateral-distal sensor than both the anterior-distal sensor and the posterior-distal sensor, (2) closer to both the anterior-distal sensor and the posterior-distal sensor than the medial-distal sensor, (3) closer to both the anterior-proximal sensor and the posterior-proximal sensor than the medial-proximal sensor, and (4) closer to the medial-proximal sensor than the medial-distal sensor; (q) the electrode relative position of the lateral-proximal electrode is (1) closer to the lateral-distal electrode than both the anterior-distal electrode and the posterior-distal electrode, (2) closer to both the anterior-distal electrode and the posterior-distal electrode than the medial-distal electrode, (3) closer to both the anterior-proximal electrode and the posterior-proximal electrode than the medial-proximal electrode, and (4) closer to the medial-proximal electrode than the medial-distal electrode; (r) the sensor relative position of the lateral-distal sensor is (1) closer to the lateral-proximal sensor than both the anterior-proximal sensor and the posterior-proximal sensor, (2) closer to both the anterior-proximal sensor and the posterior-proximal sensor than the medial-proximal sensor, (3) closer to both the anterior-distal sensor and the posterior-distal sensor than the medial-distal sensor, and (4) closer to the medial-distal sensor than the medial-proximal sensor; and(s) the electrode relative position of the lateral-distal electrode is (1) closer to the lateral-proximal electrode than both the anterior-proximal electrode and the posterior-proximal electrode, (2) closer to both the anterior-proximal electrode and the posterior-proximal electrode than the medial-proximal electrode, (3) closer to both the anterior-distal electrode and the posterior-distal electrode than the medial-distal electrode, and (4) closer to the medial-distal electrode than the medial-proximal electrode.

The foregoing paragraph sets forth an illustrative correlation between each sensor relative position of a sensor three-dimensional configuration and each electrode relative position of an electrode three-dimensional configuration. The sensor relative positions of a different array of sensors may correlate with the electrode relative positions of a different array of electrodes with an analogous-yet-distinct correlation, for example, to allow for different patterns of sensors and/or electrodes. A sensor relative position typically correlates with an electrode relative position, for example, such that an anterior sensor activates an anterior electrode, a posterior sensor activates a posterior electrode, a medial sensor activates a medial electrode, and a lateral sensor activates a lateral electrode. Pressing the front of a lower leg prosthesis would therefore transmit electrical current through the front of an upper residual leg, and pressing the back of a lower leg prosthesis would therefore transmit electrical current through the back of an upper residual leg. Other patterns are nevertheless compatible with the systems of this disclosure. Without limiting this specification or any patent claim that matures from this disclosure, correlation between the relative positions of the sensors and paired electrodes may facilitate topographic mapping and more-effectively treat phantom limb syndrome.

In some embodiments, the sensor three-dimensional configuration defines a sensor surface; the electrode three-dimensional configuration defines an electrode surface; and closeness is measured along the sensor surface and the electrode surface and not in Cartesian space. In some embodiments, the sensor surface is a surface of the cover. In some specific embodiments, the sensor surface is an outer surface of the cover. In some embodiments, the electrode surface is a surface of the liner. In some specific embodiments, the electrode surface is an inner surface of the liner.

The adjectives anterior, lateral, posterior, medial, distal, and proximal indicate (1) sensor relative positions of sensors relative to both a cover (or prosthesis) and other sensors and also (2) electrode relative positions of electrodes relative to both a liner (or residual limb) and other electrodes. An anterior-distal sensor is closer to the front of a cover (or prosthesis), for example, than lateral-distal, posterior-distal, and medial-distal sensors. An anterior-distal sensor is lower on a leg or arm prosthetic cover (or leg or arm prosthesis), for example, than an anterior-proximal sensor.

The terms anterior-proximal sensor, anterior-distal sensor, lateral-proximal sensor, lateral-distal sensor, posterior-proximal sensor, posterior-distal sensor, medial-proximal sensor, medial-distal sensor, and the like shall (1) only be construed to identify sensor relative positions, (2) shall not be construed to imply a sensor three-dimensional configuration such as by implying a regular grid, and (3) shall not to be construed to imply the existence or absence of any other sensor of an array of sensors.

The terms anterior-proximal electrode, anterior-distal electrode, lateral-proximal electrode, lateral-distal electrode, posterior-proximal electrode, posterior-distal electrode, medial-proximal electrode, medial-distal electrode, and the like shall (1) only be construed to identify electrode relative positions, (2) shall not be construed to imply an electrode three-dimensional configuration such as by implying a regular grid, and (3) shall not to be construed to imply the existence or absence of any other electrode of an array of electrodes.

In some embodiments, each sensor corresponds to exactly two electrodes, and each sensor-electrode pair consists of (1) a sensor and (2) two electrodes that correspond to the sensor. In some specific embodiments, each sensor corresponds to exactly two electrodes, and each sensor-electrode pair consists of (1) a sensor and (2) two electrodes that correspond to the sensor, wherein one of the two electrodes is a positive electrode that is configured to transmit electrical current and the other of the two electrodes is a negative electrode that is configured to receive the electrical current from the positive electrode. In some very specific embodiments, each sensor corresponds to exactly two electrodes, and each sensor-electrode pair consists of (1) a sensor and (2) two electrodes that correspond to the sensor, wherein one of the two electrodes is a positive electrode that is configured to transmit electrical current to a residual limb and the other of the two electrodes is a negative electrode that is configured to receive the electrical current from the positive electrode through the residual limb.

In some embodiments, the array of electrodes comprises at least one ring of electrodes, wherein a ring of electrodes consists of four or more electrodes that are each paired with exactly two other electrodes of the ring. In some specific embodiments, the array of electrodes comprises at least two, three, four, five, or six rings of electrodes. In some very specific embodiments, the array of electrodes comprises at least eight electrodes and at least six rings of electrodes. An anterior-proximal electrode, anterior-distal electrode, lateral-proximal electrode, and lateral-distal electrode are a ring of electrodes, for example, if the anterior-proximal and lateral-distal electrodes are each paired with the anterior-distal and lateral-proximal electrodes.

In some embodiments, at least one of the rings of electrodes are configured to encircle the residual limb. An anterior-distal electrode, lateral-distal electrode, posterior-distal electrode, and medial-distal electrode are a ring of electrodes configured to encircle the residual limb, for example, if the anterior-distal and posterior-distal electrodes are each paired with the lateral-distal and medial-distal electrodes. In some specific embodiments, at least two of the rings of electrodes are configured to encircle the residual limb.

In some embodiments, the array of sensors comprises one, two, three, four, five, six, seven, or each of an anterior-proximal sensor, an anterior-distal sensor, a lateral-proximal sensor, a lateral-distal sensor, a posterior-proximal sensor, a posterior-distal sensor, a medial-proximal sensor, and a medial-distal sensor.

In some embodiments, the array of electrodes comprises one, two, three, four, five, six, seven, or each of an anterior-proximal electrode, an anterior-distal electrode, a lateral-proximal electrode, a lateral-distal electrode, a posterior-proximal electrode, a posterior-distal electrode, a medial-proximal electrode, and a medial-distal electrode.

In some embodiments, the sensor-electrode pairs comprise one, two, three, four, five, six, seven, or each of an anterior-proximal pair that comprises the anterior-proximal sensor and the anterior-proximal electrode, an anterior-distal pair that comprises the anterior-distal sensor and the anterior-distal electrode, a lateral-proximal pair that comprises the lateral-proximal sensor and the lateral-proximal electrode, a lateral-distal pair that comprises the lateral-distal sensor and the lateral-distal electrode, a posterior-proximal pair that comprises the posterior-proximal sensor and the posterior-proximal electrode, a posterior-distal pair that comprises the posterior-distal sensor and the posterior-distal electrode, a medial-proximal pair that comprises the medial-proximal sensor and the medial-proximal electrode, and a medial-distal pair that comprises the medial-distal sensor and the medial-distal electrode. Each of the sensor-electrode pairs identified in the preceding sentence also include an additional electrode; the anterior-proximal pair also comprises, for example, one or more of a second anterior-proximal electrode, the anterior-distal electrode, the lateral-proximal electrode, the medial-proximal electrode, or an entirely different electrode.

In some embodiments, each sensor of the array of sensors is in communication with two or more electrodes of the array of electrodes such that the two or more electrodes are configured to transmit and receive electrical current through the residual limb when each of (1) the sensor senses force or pressure; (2) the two or more electrodes are in electrical communication with the residual limb; and (3) the prosthesis is detached from the residual limb. Such configurations allow an amputee to transmit electrical current through his or her residual limb, optionally to treat symptoms of phantom limb syndrome, when the amputee is not wearing a prosthesis with the cover, for example, after the amputee has removed such a prosthesis to sleep.

In some embodiments, an array of sensors comprises at least 4, 5, 6, 7, 8, 9, 10, 11, 12, 14, 16, 18, 20, 24, 28, or 32 sensors. In some specific embodiments, an array of sensors comprises at least 4 and up to 128 sensors. In some specific embodiments, an array of sensors comprises 4, 5, 6, 7, 8, 9, 10, 11, 12, 14, 16, 18, 20, 24, 28, 32, 64, or 128 sensors. In some very specific embodiments, an array of sensors comprises 4, 5, 6, 7, 8, 9, 10, 11, 12, 14, 16, 18, 20, 24, 28, 32, 64, or 128 sensors, and the system comprises a plurality of additional sensors that are not included in the array of sensors.

In some embodiments, the system comprises one or more sensors that are not included in the array of sensors. The unincluded one or more sensors may be, for example, sensors that are not used to detect force or pressure or sensors that a prospective infringer of one or more patent claims that mature from this disclosure might contemplate including in a system in an attempt to develop a legal theory of non-infringement.

In some embodiments, the system comprises a controller, wherein the controller is in communication with the array of electrodes such that the controller can bypass the array of sensors to cause each electrode of the array of electrodes to transmit or receive electrical current to or from a residual limb of an amputee when the electrode is in electrical communication with the residual limb. Such a controller can allow an amputee to transmit electrical current through his or her residual limb when the amputee is not wearing a prosthesis with the cover, for example, after the amputee has removed such a prosthesis to sleep. A controller can also allow an amputee to run programs that specifically treat phantom limb syndrome. An amputee might develop a specific pattern of transmitting electrical current through his or her residual limb that is particularly efficacious at treating phantom limb syndrome, the system might track an amputee's use of the system and develop a specific pattern that displays a high probability of efficaciously treating phantom limb syndrome, or crowd-sourced use records from a plurality of amputees or other data might identify a specific pattern that displays a high probability of efficaciously treating phantom limb syndrome, and a program on a controller can drive the array of electrodes to implement the specific pattern. Such a controller may optionally be an electrode controller or a secondary controller as described herein.

In some embodiments, the system comprises a secondary controller in wireless communication with the array of electrodes such that the secondary controller can bypass the array of sensors to cause each electrode of the array of electrodes to transmit or receive electrical current to or from the residual limb when the array of electrodes is in electrical communication with the residual limb.

In some embodiments, the secondary controller is a computing device. In some specific embodiments, the secondary controller is a mobile computing device. In some very specific embodiments, the secondary controller is a cellphone.

In some embodiments, the secondary controller is in wireless communication with the array of electrodes. In some specific embodiments, the secondary controller is in wireless communication with an electrode controller. In some very specific embodiments, the secondary controller is in wireless communication with an electrode controller that controls the array of electrodes.

In some embodiments, the wireless communication is mediated by one or both of a Bluetooth or Wi-Fi connection between the secondary controller and the array of electrodes. In some specific embodiments, the wireless communication is mediated by one or both of a Bluetooth or Wi-Fi connection between the secondary controller and the array of electrodes, which is mediated by an electrode controller that controls the array of electrodes.

In some embodiments, the secondary controller is in wireless communication with the electrode controller.

In some embodiments, the cover is configured to attach to outer surfaces of different prostheses that have a variety of different shapes, and the cover is configured to adapt to the variety of different shapes such that each sensor relative position remains constant for different shapes. In some specific embodiments, the cover is configured to attach to outer surfaces of different prostheses that have a variety of different shapes, and the cover is configured to adapt to the variety of different shapes such that each sensor three-dimensional configuration remains constant for different shapes.

In some embodiments, the cover has a shape of a missing body part. In some specific embodiments, the cover has a shape of a missing body part, and the sensor three-dimensional configuration comprises the shape of the missing body part. Without limiting this specification or any patent claim that matures from this disclosure, a cover that has a shape of a missing part and a sensor three-dimensional configuration that comprises the shape more favorably induces neuroplasticity in the somatosensory cortex of the brain of an amputee than other shapes, which more efficaciously treats phantom limb syndrome.

In some embodiments, the system lacks any sensor ability to sense a relative position of a prosthesis. In some specific embodiments, the array of sensors is generally configured to sense pressure and/or force from touch, and the array of sensors is not generally configured to sense the position or performance of a prosthesis.

In some embodiments, the system lacks any mechanical capability to move a prosthesis. In some specific embodiments, the system is generally unrelated to the mechanical properties of a prosthesis, for example, to support movement, positioning, or load.

In some embodiments, the system lacks any structural ability to support bodyweight of an amputee. In some specific embodiments, the system is generally unrelated to the structural properties of a prosthesis, for example, to support movement, positioning, or load.

FIG. 1 depicts a system 100, which comprises a prosthetic liner 101 that comprises an embedded array of electrodes 102*a-d*. The prosthetic liner 101 receives a residual limb (not shown) such that the liner 101 fits underneath a region of a prosthesis 103 that also receives the residual limb. Prosthetic liners provide suspension, protection and cushion to a residual limb of an amputee.

Each electrode 102*a-d* of the array of electrodes 102*a-d* in the prosthetic liner 101 is in electrical communication with an electrode controller 104, which electrical communication is mediated by wires 105 that are also embedded in the prosthetic liner 101. In some embodiments, the electrical communication can be mediated by conductors other than wires, such as conductive material.

The prosthetic liner may comprise a tube comprising a wall, an edge that defines a terminus of the wall, an open end bounded by the edge, and a void space defined by the wall, wherein the void space configured to receive the residual limb through the open end. In some specific embodiments, the tube comprises a closed end that is continuous with the wall, for example, such that the void space is defined by the closed end, the wall, and the open end.

In some embodiments, the liner generally comprises a concave interior surface of the tube and a convex exterior surface of the tube, wherein the edge defines a boundary between the concave interior surface and the convex exterior surface.

FIG. 1 depicts a system 100, which also comprises a cover 106 that comprises an embedded array of sensors 107*a-d*. The cover 106 fits over a region of the prosthesis 103 that replaces a missing limb and is optionally attached to the prosthesis 103 with a polymer foam (not shown) that fills void space between the cover 106 and the prosthesis 103. The sensors 107*a-d* are in communication with a sensor controller 108 that interfaces with the electrode controller 104.

FIG. 1 depicts a wireless, Bluetooth-mediated interface 109 between the sensor controller 108 and the electrode controller 104. The wireless, Bluetooth-mediated interface 109 between the sensor controller 108 and the electrode controller 104 allows amputees to contact the sensors 107*a-d* to activate electrodes 102*a-d* of the array of electrodes 102*a-d* to stimulate their residual limbs even when an amputee is not wearing the prosthetic 103 and cover 106, for example, such as when the amputee has removed the prosthetic 103 to sleep. In other embodiments, the system 100 lacks a sensor controller 108, and sensors 107*a-d* are connected directly to the electrode controller 104.

The liner 101 of FIG. 1 comprises a substrate 110 that houses the embedded array of electrodes 102*a-d*. Also shown in FIG. 1 is a joint 111 of the prosthesis 103, an outer layer 112 of the cover 106, which outer layer 112 is shown in an exploded view, and sheathing 113 that bundles wires 105 that exit the liner 101.

The electrodes 102*a-d* depicted in FIG. 1 include an anterior-lateral-proximal electrode 102*a*, an anterior-lateral-distal electrode 102*b*, a posterior-lateral-distal electrode 102*c*, and a posterior-lateral-proximal electrode 102*d*. The opposite side of the liner might include, for example, an anterior-medial-proximal electrode, an anterior-medial-distal electrode, a posterior-medial-distal electrode, and a posterior-medial-proximal electrode in the mirror image of the depicted side.

The sensors 107*a-d* depicted in FIG. 1 include an anterior-lateral-proximal sensor 107*a*, an anterior-lateral-distal sensor 107*b*, a posterior-lateral-distal sensor 107*c*, and a posterior-lateral-proximal sensor 107*d*. The opposite side of the cover might include, for example, an anterior-medial-proximal sensor, an anterior-medial-distal sensor, a posterior-medial-distal sensor, and a posterior-medial-proximal sensor in the mirror image of the depicted side.

In some embodiments, pressing the anterior-lateral-proximal sensor 107*a* will transmit electricity through a residual limb between the anterior-lateral-proximal electrode 102*a* and at least one other electrode.

In some embodiments, pressing the anterior-lateral-distal sensor 107*b* will transmit electricity through a residual limb between the anterior-lateral-distal electrode 102*b* and at least one other electrode.

In some embodiments, pressing the posterior-lateral-distal sensor 107*c* will transmit electricity through a residual limb between the posterior-lateral-distal electrode 102*c* and at least one other electrode.

In some embodiments, pressing the posterior-lateral-proximal sensor 107*d* will transmit electricity through a residual limb between the posterior-lateral-proximal electrode 102*d* and at least one other electrode.

In some specific embodiments, (1) pressing both the anterior-lateral-proximal sensor 107*a* and the anterior-medial-proximal sensor (not shown) will transmit electricity between the anterior-lateral-proximal electrode 102*a* and the anterior-medial-proximal electrode (not shown); (2) pressing both the anterior-medial-proximal sensor (not shown) and the posterior-medial-proximal sensor (not shown) will transmit electricity between the anterior-medial-proximal electrode (not shown) and the posterior-medial-proximal electrode (not shown); (3) pressing both the posterior-medial-proximal sensor (not shown) and the posterior-lateral-proximal sensor 107*d* will transmit electricity between the posterior-medial-proximal electrode (not shown) and the posterior-lateral-proximal electrode 102*d*; and (4) pressing both the posterior-lateral-proximal sensor 107*d* and the anterior-lateral-proximal sensor 107*a* will transmit electricity between the posterior-lateral-proximal electrode 102*d* and the anterior-lateral-proximal electrode 102*a*, thereby creating a "ring" around the residual limb. The electricity may be transmitted simultaneously, in series, or otherwise. In the alternative, a secondary controller (such as a mobile app on a wireless device) may be used to bypass the sensors to arrive at a similar pattern of electrical transmission through the residual limb.

In some specific embodiments, (1) pressing both the anterior-lateral-proximal sensor 107*a* and the anterior-lateral-distal sensor 107*b* will transmit electricity between the anterior-lateral-proximal electrode 102*a* and the anterior-lateral-distal electrode 102*b*; (2) pressing both the anterior-lateral-distal sensor 107*b* and the posterior-lateral-distal sensor 102*c* will transmit electricity between the anterior-lateral-distal electrode 102*b* and the posterior-lateral-distal electrode 102*c*; (3) pressing both the posterior-lateral-distal sensor 102*c* and the posterior-lateral-proximal sensor 107*d* will transmit electricity between the posterior-lateral-distal electrode 102*c* and the posterior-lateral-proximal electrode 102*d*; and (4) pressing both the posterior-lateral-proximal sensor 107*d* and the anterior-lateral-proximal sensor 107*a* will transmit electricity between the posterior-lateral-proximal electrode 102d and the anterior-lateral-proximal electrode 102a, thereby creating a "ring" on the lateral side of the residual limb. The electricity may be transmitted simultaneously, in series, or otherwise. In the alternative, a secondary controller (such as a mobile app on a wireless device) may be used to bypass the sensors to arrive at a similar pattern of electrical transmission through the residual limb.

Figure 2:
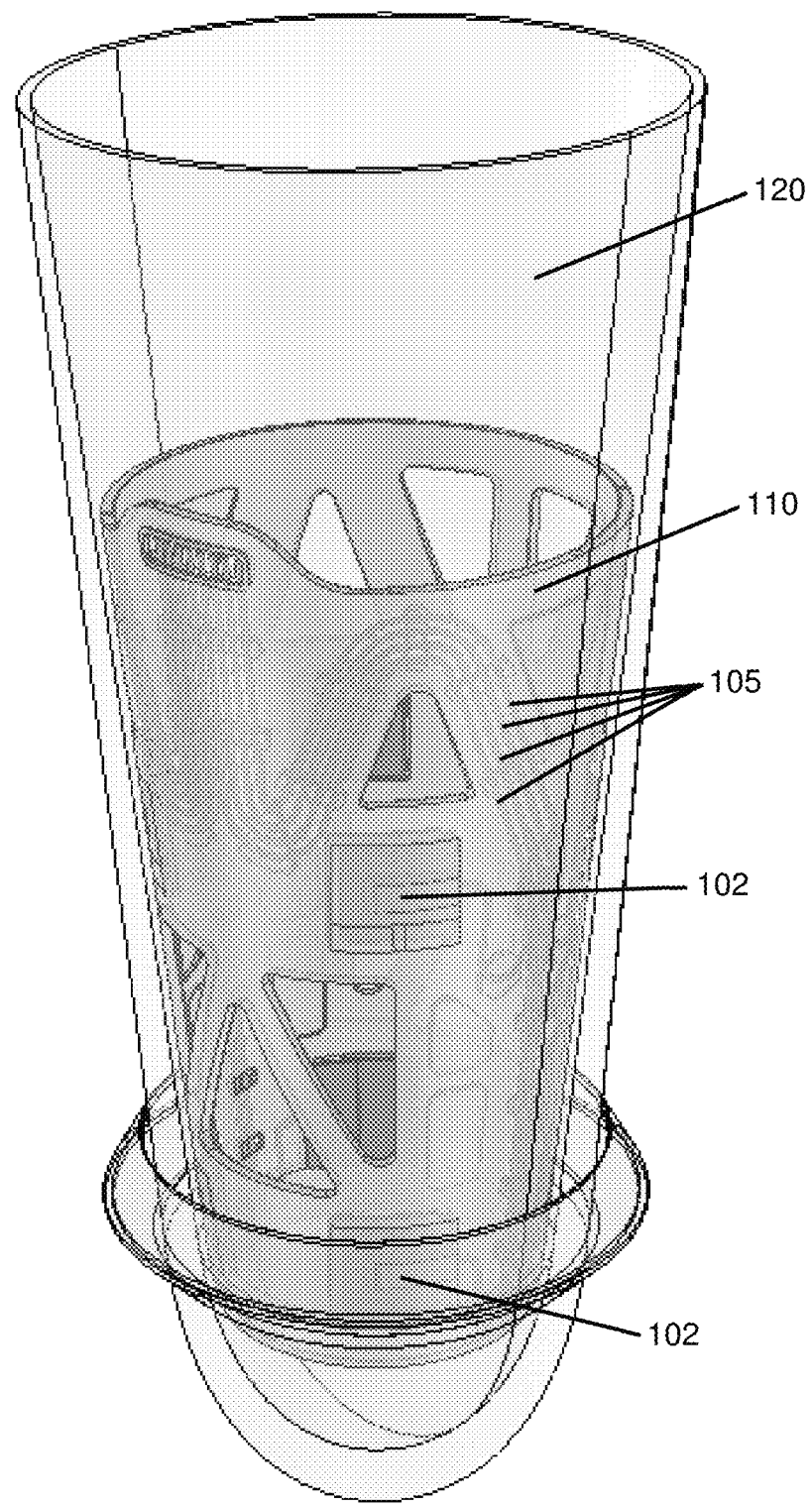
FIG. 2 depicts a substrate and a mold for manufacturing a liner.

FIG. 2 depicts a substrate 110 with an embedded array of electrodes 102 and embedded wires 105. In some embodiments, the substrate 110 may be incorporated into a prosthetic liner. In some embodiments, the prosthetic liner may be overmolded onto or otherwise embedded into or attached to the substrate.

Referring to FIG. 2, the substrate 110 is positioned within a mold 120. In some embodiments, liquid silicone (not shown) may be poured into the mold 120 to form a liner (not shown) that comprises the embedded array of electrodes 102 and embedded wires 105.

In some embodiments, the substrate is a fabric, such as a fabric mesh array configured to stimulate partial or full coverage around the residual limb.

In some embodiments, the substrate may include a conductor. The conductor may be any component that carries electrical current from a power source to the electrodes in the substrate. The conductor may be wires that are at least partially incorporated into the substrate. In some embodiments, the conductor may be a conductive material (e.g., an elastomer).

Figure 3:
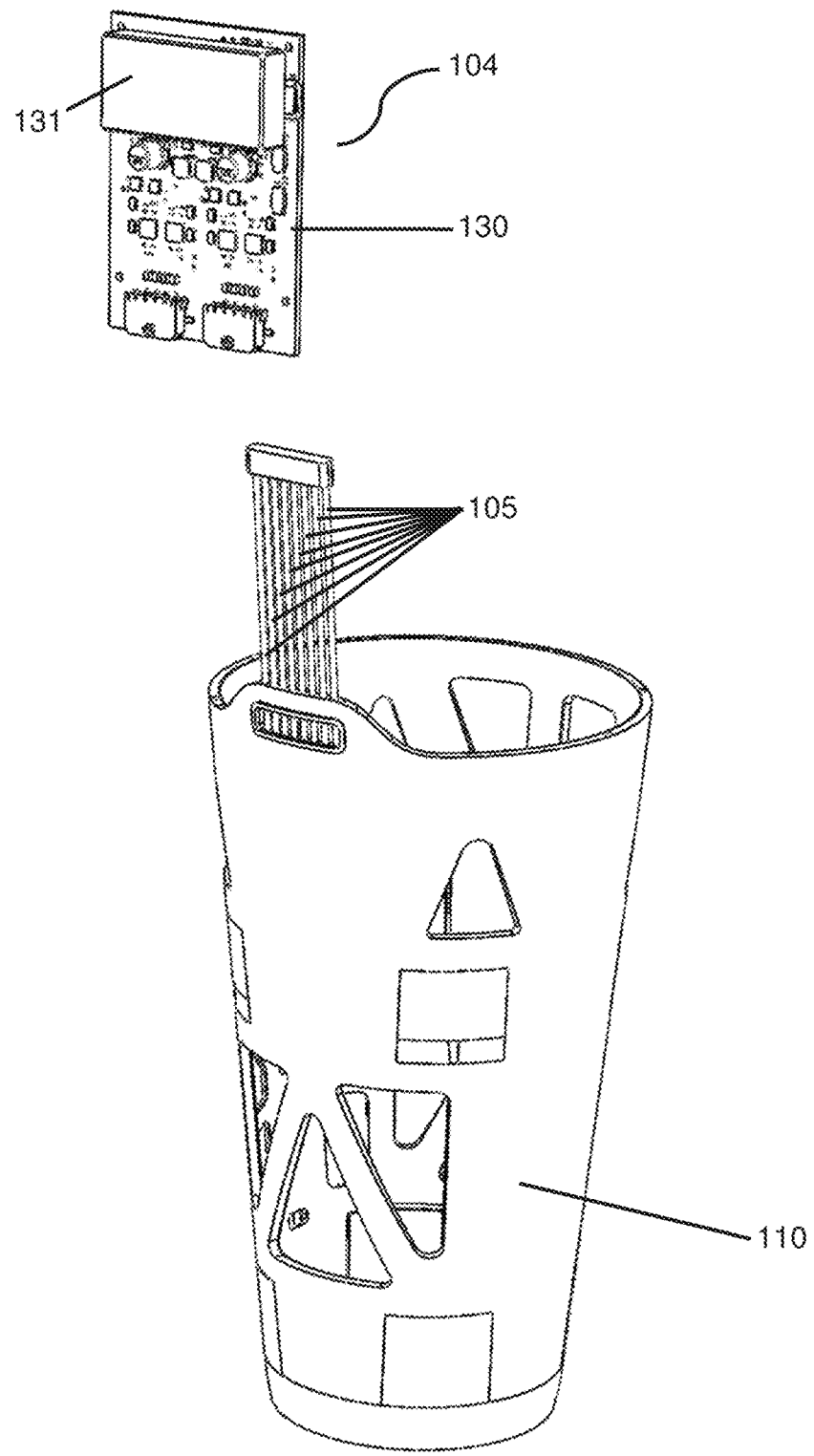
FIG. 3 depicts a substrate and an electrode controller.
Figure 4:
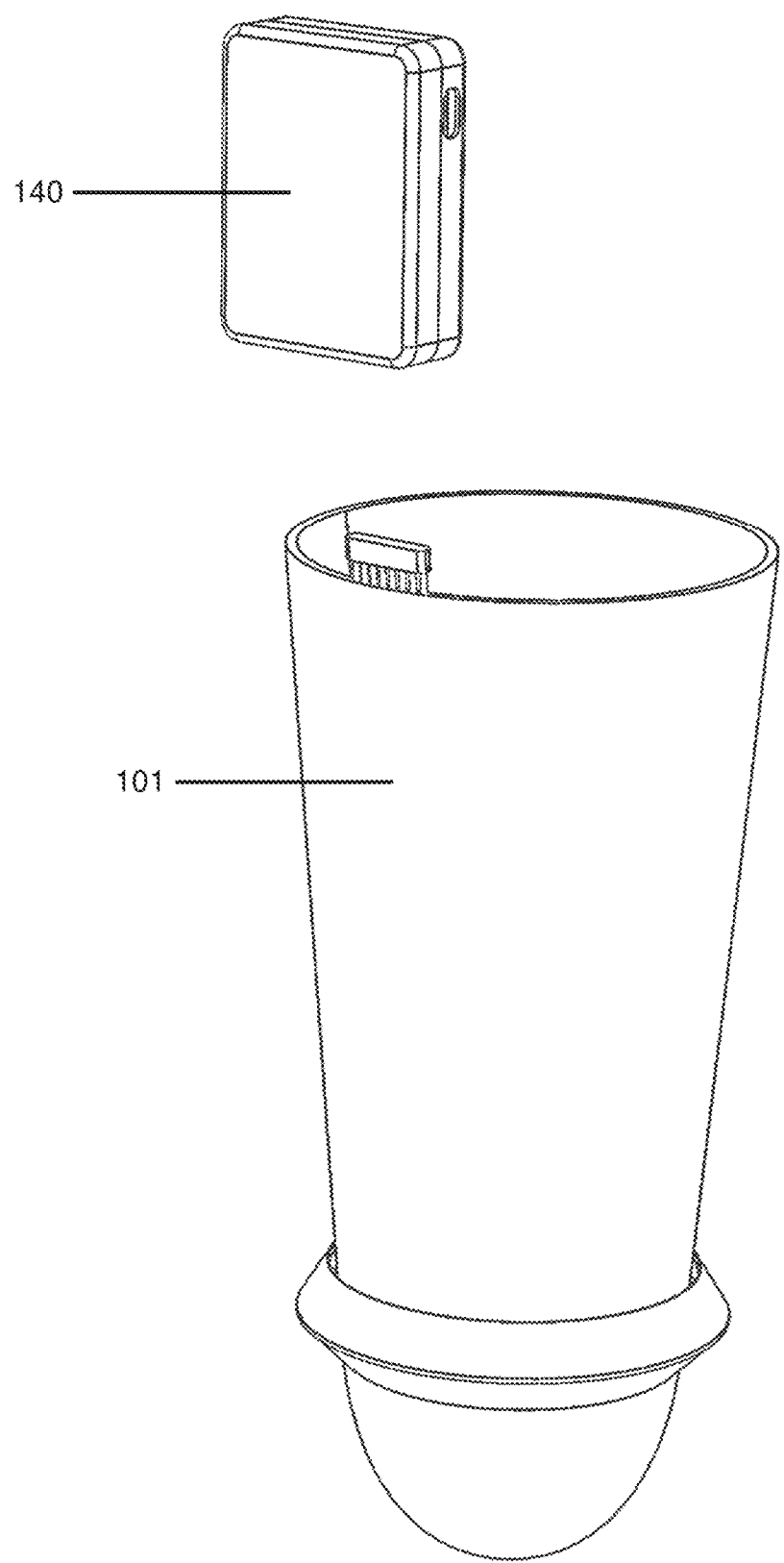
FIG. 4 depicts a liner and a housing that houses an electrode controller.

FIG. 3 depicts a substrate 110 with an embedded array of electrodes (not shown) and embedded wires 105. FIG. 3 also depicts an electrode controller 104, which comprises a printed circuit board assembly 130 and a battery 131 in electrical communication with the printed circuit board assembly 130. When the electrode controller 104 is in electrical communication with the embedded wires 105, then a microprocessor (not shown) of the printed circuit board assembly 130 of the electrode controller 104 controls the transmission of electrical current between the battery 131 and the embedded wires 105 to control whether an electrode of the array of electrodes will transmit electrical current, which the electrode receives from the battery 131, and whether an electrode of the array of electrodes will receive electrical current, which the electrode transmits to the battery 131. FIG. 4 depicts a liner 101 that comprises the substrate (not shown) of FIG. 3 and an electrode controller housing 140 that houses the electrode controller (not shown) of FIG. 3.

Figure 5:
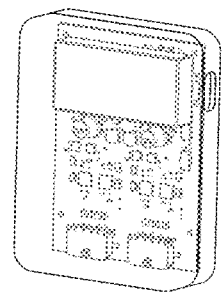
FIG. 5 depicts the liner and housing of FIG. 4 with partial transparency such that a substrate and electrode controller are visible.
Figure 5:
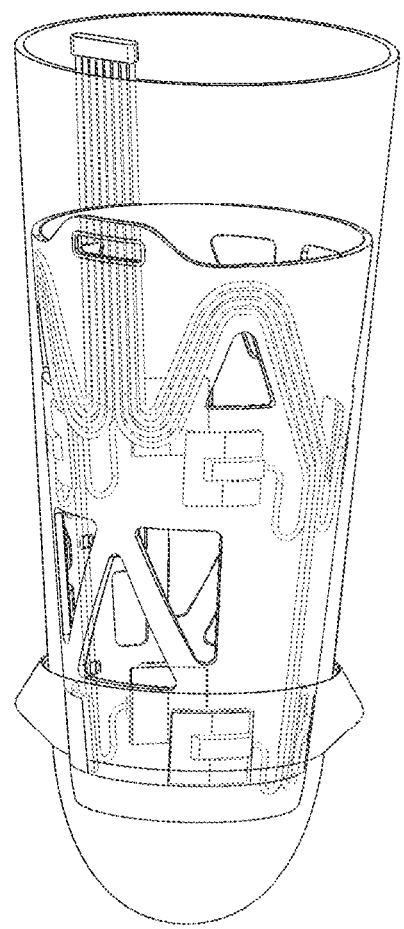

FIG. 5 depicts the liner 101 and electrode controller housing 140 of FIG. 4 with partial transparency such that the substrate 110 and electrode controller 104 are visible.

Figure 6:
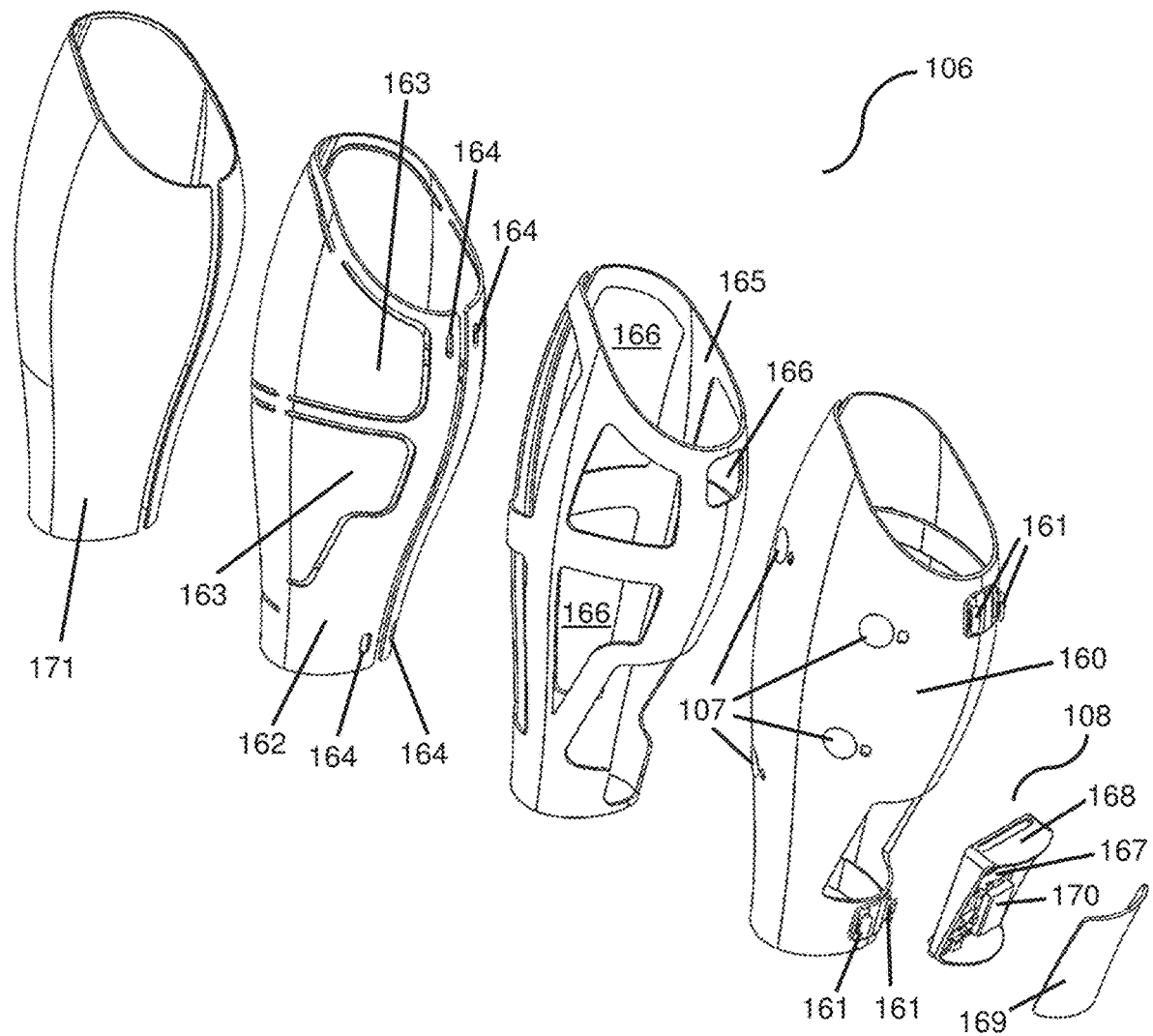
FIG. 6 depicts an exploded view of a cover configured to fit over a prosthesis.

FIG. 6 depicts an exploded view of a cover 106, which comprises sensors 107. The cover 106 comprises an inner layer 160, which is depicted with embedded sensors 107 that are configured to sense a modality (e.g., force or pressure). The inner layer 160 may be manufactured, for example, from plastic. The inner layer 160 optionally comprises one or more tabs 161 or other attachment feature to receive an outer layer 162. The outer layer 162 may be manufactured, for example, from plastic. The outer layer 162 may optionally have actuators 163, each of which is configured to press against one or more sensors 107. Each actuator 163 may be configured, for example, as a flex panel that has a larger surface area than any of the sensors 107 such that depressing any portion of an actuator 163 transduces a modality (e.g., force or pressure) to one or more of the smaller sensors 107. The outer layer 162 optionally comprises one or more slots 164 or other attachment feature to receive the inner layer 160. As shown in FIG. 6, the outer layer 162 comprises four slots 164 that are shaped to receive four tabs 161 of the inner layer 160 to attach the outer layer 162 and the inner layer 160. A mechanical attachment feature, such as a tab, may include a detent, barb, or other catch or clamp feature to inhibit detachment of the inner layer 160 and the outer layer 162.

The cover 106 may optionally comprise a spacer 165 between the inner layer 160 and the outer layer 162. The spacer 165 may comprise, for example, foam. The spacer 165 may include one or more void spaces 166. The one or more void spaces 166 can allow, for example, an actuator 163 to contact a sensor 107. The one or more void spaces 166 can also allow, for example, an attachment feature such as the one or more tabs 161 and the one or more slots 164 to attach the inner layer 160 and the outer layer 162.

The cover 106 may optionally include a sensor controller 108. A sensor controller 108 typically comprises a printed circuit board assembly 167 that comprises an interface and a microprocessor. The microprocessor is configured, for example, to receive signals from the sensors 107 and direct the interface to transmit a corresponding signal to the array of electrodes or a controller thereof. The interface may be, for example, a wireless interface such as a combined Wifi Bluetooth chip. The precise type of interface is not limiting and generally depends upon market factors including the manufacturer suggested retail price of the system. The controller 108 typically comprises a controller housing 168, which may optionally comprise an access panel 169 to allow access to the printed circuit board assembly 167. A sensor controller 108 typically either comprises or is otherwise in electrical communication with a power source, which is typically a battery 170.

In some embodiments, a cover lacks a dedicated sensor controller (not shown). A system may comprise, for example, a hardwired interface between a cover and a liner such that a sensor controller is unnecessary.

The cover 106 may optionally comprise an outer surface 171, which may comprise, for example, foam and/or a favorable texture for physical interaction with actuators 163.

Figure 7:
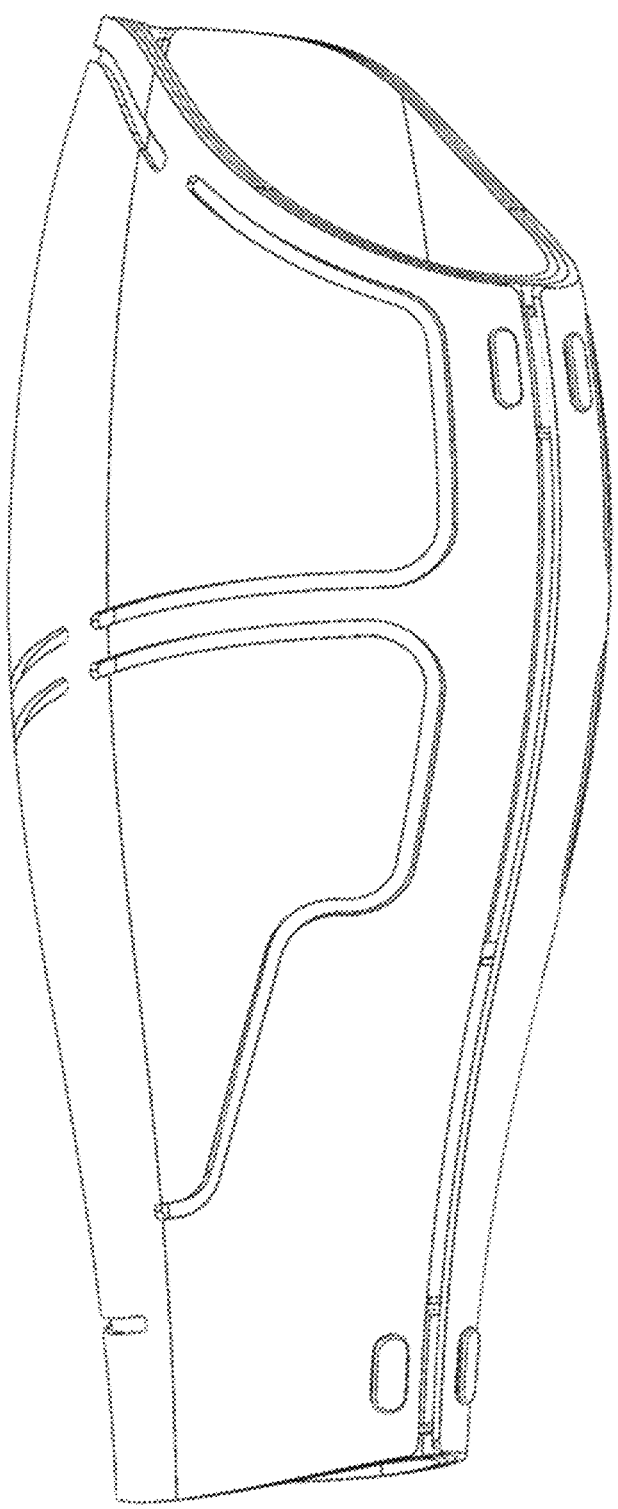
FIG. 7 depicts the cover of FIG. 6 in an assembled configuration without an outer surface.

FIG. 7 depicts a cover 106 of FIG. 6 in an assembled configuration without the outer surface (not shown). The four tabs 161 of the inner layer 160 attach the outer layer 162 and the inner layer 160. The outer layer 162 conceals the controller housing 168.

Figure 8:
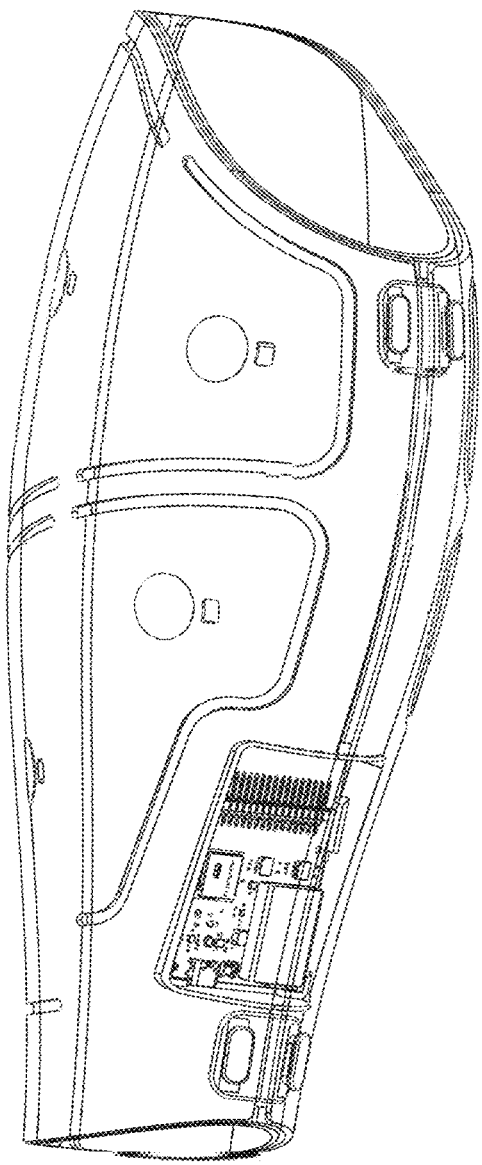
FIG. 8 depicts the cover of FIGS. 6 & 7 in an assembled configuration without the outer surface, in which an outer layer is semi-transparent and a spacer is transparent to show underlying sensors and a sensor controller.

FIG. 8 depicts the cover 106 of FIGS. 6 & 7 in an assembled configuration without the outer surface (not shown), wherein the outer layer 162 is semi-transparent and the spacer 165 is transparent to show the underlying sensors 107 and printed circuit board assembly 167.

Figure 9:
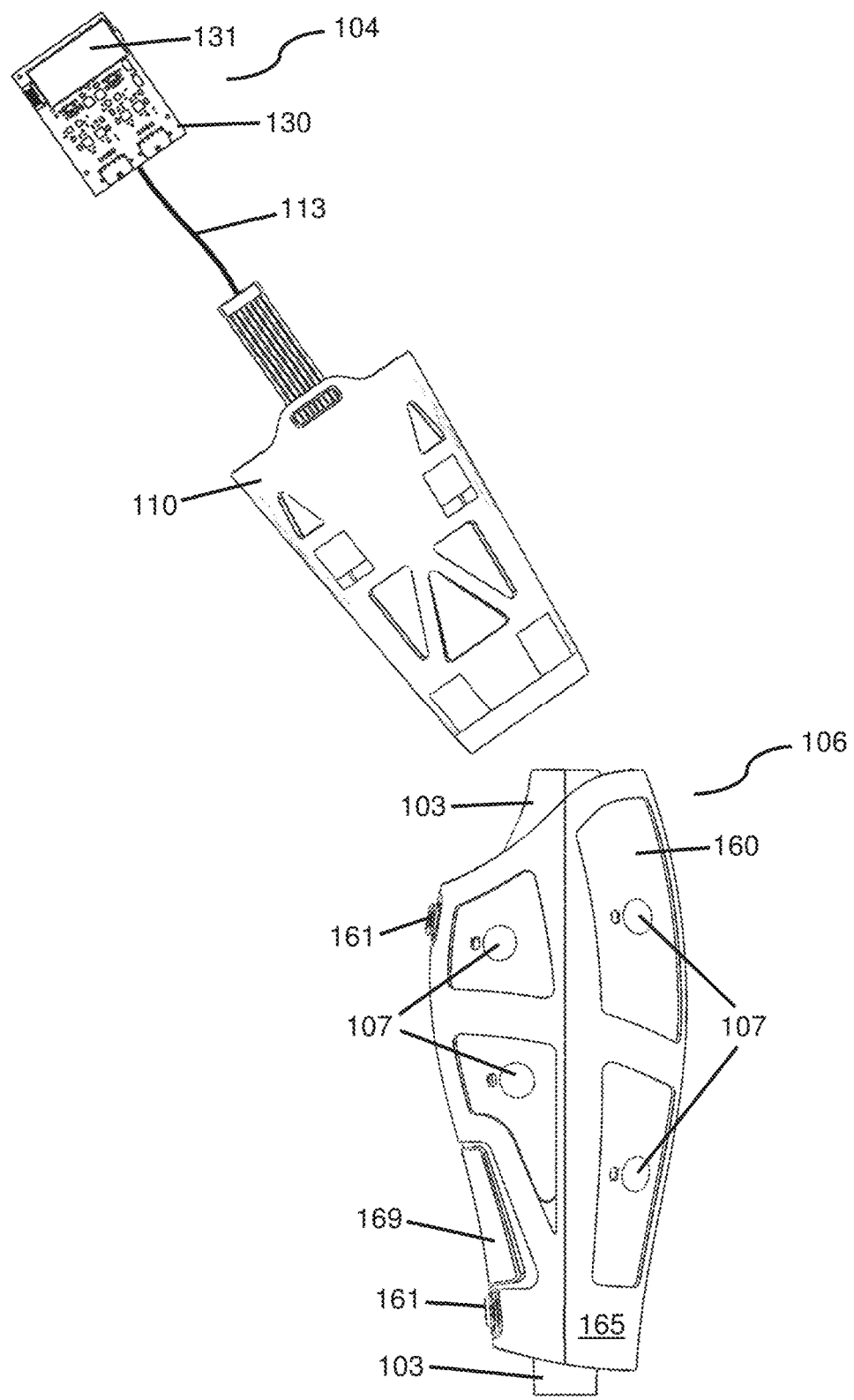
FIG. 9 depicts the substrate and electrode controller of FIG. 3 and a partially-assembled cover according to FIG. 6-8.

FIG. 9 depicts the electrode controller 104 and substrate 110 of FIG. 3 and a partially-assembled cover 106 of FIG. 6-8.

Various aspects of this disclosure relate to a method of using a system described anywhere in this disclosure.

In some embodiments, the method is a method to modulate nerve activation in a residual limb of an amputee.

Each amputee has a missing body part. In some embodiments, the amputee presents with phantom limb syndrome.

In some embodiments, the system comprises a cover, and the method comprises attaching the cover to a prosthesis. In some specific embodiments, the method comprises inserting a foam between the cover and the prosthesis to attach the cover to the prosthesis. In some very specific embodiments, the method comprises inserting an expandable foam between the cover and the prosthesis to attach the cover to the prosthesis.

In some embodiments, the system comprises a liner, and the method comprises attaching the liner to the residual limb. In some specific embodiments, the liner comprises an array of electrodes, and the method comprises attaching the liner to the residual limb such that each electrode of the array of electrodes is in electrical communication with the residual limb. In some very specific embodiments, attaching the liner to the residual limb comprises attaching each electrode of the array of electrodes to the residual limb such that each electrode is in electrical communication with the residual limb.

In some embodiments, the method comprises contacting the residual limb with a conductive gel to facilitate electrical communication between each electrode of the array of electrodes and the residual limb.

In some embodiments, the method comprises attaching the prosthesis to the residual limb. In some specific embodiments, the method comprises attaching the prosthesis to the residual limb subsequent to attaching the cover to the prosthesis. In some specific embodiments, the method comprises attaching the prosthesis to the residual limb such that the prosthesis fits over a liner. In some very specific embodiments, the method comprises attaching the prosthesis to the residual limb subsequent to attaching the cover to the prosthesis and subsequent to attaching the liner to the residual limb such that the prosthesis fits over the liner.

In some embodiments, the system comprises an array of sensors, and the method comprises contacting one or more of the sensors. In some specific embodiments, the cover comprises an array of sensors, and the method comprises contacting one or more sensors. In some very specific embodiments, contacting the one or more sensors comprises applying at least one modality (e.g., one or both of force and pressure) to the one or more sensors.

In some embodiments, the method comprises contacting one or more of the sensors after attaching the cover to the prosthesis. In some embodiments, the method comprises contacting one or more sensors after attaching the prosthesis to the residual limb. In some specific embodiments, the method comprises contacting one or more sensors after both attaching the cover to the prosthesis and attaching the prosthesis to the residual limb. In some very specific embodiments, the method comprises contacting one or more sensors after attaching the liner to the residual limb, attaching the cover to the prosthesis, and attaching the prosthesis to the residual limb.

In some embodiments, the method comprises detaching the prosthesis from the residual limb and contacting the one or more sensors after detaching the prosthesis from the residual limb. Methods of this disclosure advantageously allow an amputee to transmit electrical current through his or her residual limb, optionally to treat symptoms of phantom limb syndrome, when the amputee is not wearing a prosthesis with the cover, for example, after the amputee has removed such a prosthesis to sleep.

In some embodiments, contacting the one or more sensors causes an electrode of the array of electrodes to transmit electrical current to the residual limb and another electrode of the array of electrodes to receive the electrical current from the residual limb.

In some embodiments, contacting the one or more sensors after attaching the cover to the prosthesis causes an electrode of the array of electrodes to transmit electrical current to the residual limb and another electrode of the array of electrodes to receive the electrical current from the residual limb. In some embodiments, contacting the one or more sensors after attaching the prosthesis to the residual limb causes an electrode to transmit electrical current to the residual limb and another electrode to receive the electrical current from the residual limb. In some specific embodiments, contacting the one or more sensors after both attaching the cover to the prosthesis and attaching the prosthesis to the residual limb causes an electrode to transmit electrical current to the residual limb and another electrode to receive the electrical current from the residual limb. In some very specific embodiments, contacting the one or more sensors after attaching the liner to the residual limb, attaching the cover to the prosthesis, and attaching the prosthesis to the residual limb causes an electrode to transmit electrical current to the residual limb and another electrode to receive the electrical current from the residual limb.

In some embodiments, contacting the one or more sensors after detaching the prosthesis from the residual limb causes an electrode to transmit electrical current to the residual limb and another electrode to receive the electrical current from the residual limb.

In some embodiments, the method comprises stimulating Aβ nerve fibers in the residual limb. In some specific embodiments, the method comprises stimulating myelinated Aβ nerve fibers in the residual limb, wherein transmitting electrical current to the residual limb stimulates the myelinated Aβ nerve fibers in the residual limb.

In some embodiments, the method comprises modulating the activation of Aδ nerve fibers in the residual limb. In some specific embodiments, the method comprises modulating the activation of myelinated Aδ nerve fibers in the residual limb, wherein transmitting electrical current to the residual limb modulates the activation of the myelinated Aδ nerve fibers in the residual limb.

In some embodiments, the method comprises modulating the activation of C nerve fibers in the residual limb. In some specific embodiments, the method comprises modulating the activation of unmyelinated C nerve fibers in the residual limb, wherein transmitting electrical current to the residual limb modulates the activation of the unmyelinated C nerve fibers in the residual limb.

In some embodiments, the system is configured such that the electrical current treats one or more symptoms of the phantom limb syndrome. In some specific embodiments, the system is configured such that the electrical current treats one or more symptoms of the phantom limb syndrome, and contacting the one or more sensors treats the one or more symptoms by causing the transmitting of electrical current through the residual limb.

In some embodiments, the method comprises detaching the prosthesis from the residual limb and contacting the one or more sensors after detaching the prosthesis from the residual limb; and contacting the one or more sensors after detaching the prosthesis from the residual limb treats the one or more symptoms by causing the transmitting of electrical current through the residual limb.

In some embodiments, the method comprises directing the secondary controller to cause an electrode to transmit electrical current to the residual limb and another electrode to receive the electrical current from the residual limb. In some specific embodiments, the method comprises directing the secondary controller to cause an electrode to transmit electrical current to the residual limb and another electrode to receive the electrical current from the residual limb without contacting the one or more sensors (i.e., the secondary controller bypasses the array of sensors).

Directing the secondary controller may comprise, for example, pressing an icon on a touchscreen graphical user interface of the controller or secondary controller.

In some embodiments, directing the secondary controller to cause the electrode to transmit electrical current to the residual limb and another electrode to receive the electrical current from the residual limb treats the one or more symptoms by transmitting electrical current through the residual limb.

In some embodiments, the method comprises directing a secondary controller in wireless communication with the system to cause one or more positive electrodes of the array of electrodes to transmit electrical current to the residual limb and one or more negative electrodes of the array of electrodes to receive the electrical current from the residual limb. In some specific embodiments, directing the secondary controller to cause the one or more positive electrodes to transmit the electrical current and the one or more negative electrodes to receive the electrical current treats one or more symptoms of the phantom limb syndrome by transmitting the electrical current through the residual limb.

In some embodiments, the method comprises either (1) contacting one or more sensors to cause the one or more positive electrodes to transmit electrical current to the residual limb and the one or more negative electrodes to receive the electrical current from the residual limb in response to a symptom of the phantom limb syndrome or (2) directing the secondary controller to cause the one or more positive electrodes to transmit electrical current to the residual limb and the one or more negative electrodes to receive the electrical current from the residual limb in response to the symptom, and the method treats the phantom limb syndrome by transmitting the electrical current through the residual limb in response to the symptom.

In some embodiments, the method comprises transmitting electrical current through the residual limb from a positive electrode of the array of electrodes to a negative electrode of the array of electrodes periodically over a period of time such as a course of at least 28 days. In some specific embodiments, the method comprises transmitting electrical current through the residual limb from the positive electrode to the negative electrode periodically over the period of time, and the method is effective at reducing symptoms of the phantom limb syndrome as assessed with a Visual Analog Scale following the period of time.

In some embodiments, periodically means at least three times per week, at least four times per week, at least five times per week, at least six times per week, at least seven times per week, at least daily, or at least twice per day.

In some embodiments, periodically means three times per week, four times per week, five times per week, six times per week, seven times per week, daily, or twice per day.

In some embodiments, the period of time is at least one hour, at least 24 hours, at least 48 hours, at least one week, at least 28 days, at least one month, at least six months, or at least one year.

In some embodiments, the period of time is one hour, 24 hours, 48 hours, one week, 28 days, one month, six months, or one year.

In some embodiments, the method comprises contacting the one or more sensors of the array of sensors and transmitting electrical current through the residual limb from a positive electrode of the array of electrodes to a negative electrode of the array of electrodes periodically over a period of time such as a course of at least 28 days. In some specific embodiments, the method comprises contacting the one or more sensors and transmitting electrical current through the residual limb from the positive electrode to the negative electrode periodically over the period of time, and the method is effective at reducing symptoms of the phantom limb syndrome as assessed with a Visual Analog Scale following the period of time.

In some embodiments, the phantom limb syndrome has a first symptom and a second symptom.

In some embodiments, transmitting electrical current through the residual limb from a first positive electrode of the array of electrode to a first negative electrode of the array of electrodes is more effective at treating the first symptom than transmitting and receiving electrical current from other electrodes of the array of electrodes; and the method comprises transmitting electrical current through the residual limb from the first positive electrode to the first negative electrode in response to the first symptom.

In some embodiments, the first positive electrode has a first positive electrode relative position; the first negative electrode has a first negative electrode relative position; and the amputee associates the first symptom with one or both of the first positive electrode relative position and the first negative electrode relative position.

In some embodiments, transmitting electrical current through the residual limb from a second positive electrode of the array of electrode to a second negative electrode of the array of electrodes is more effective at treating the second symptom than transmitting and receiving electrical current from other electrodes of the array of electrodes, and the method comprises transmitting electrical current through the residual limb from the second positive electrode to the second negative electrode in response to the second symptom.

In some embodiments, the second positive electrode has a second positive electrode relative position; the second negative electrode has a second negative electrode relative position; and the amputee associates the second symptom with one or both of the second positive electrode relative position and the second negative electrode relative position.

In some embodiments, the method comprises contacting a first sensor of the array of sensors that corresponds to the first positive electrode and the first negative electrode in response to the first symptom.

In some embodiments, the first sensor has a first sensor relative position, and the amputee associates the first symptom with the first sensor relative position. In some specific embodiments, the first sensor has a first sensor relative position; the first positive electrode has a first positive electrode relative position; the first negative electrode has a first negative electrode relative position; and the amputee associates the first symptom with one, two, or each of the first sensor relative position, the first positive electrode relative position, and the first negative electrode relative position.

In some embodiments, the method comprises contacting a second sensor of the array of sensors that corresponds to the second positive electrode and the second negative electrode in response to the second symptom.

In some embodiments, the second sensor has a second sensor relative position, and the amputee associates the second symptom with the second sensor relative position. In some specific embodiments, the second sensor has a second sensor relative position; the second positive electrode has a second positive electrode relative position; the second negative electrode has a second negative electrode relative position; and the amputee associates the second symptom with one, two, or each of the second sensor relative position, the second positive electrode relative position, and the second negative electrode relative position.

In some embodiments, the method comprises directing the electrode controller (optionally by a secondary controller) to direct the first positive electrode to transmit electrical current to the residual limb and the first negative electrode to receive the electrical current in response to the first symptom.

In some embodiments, the method comprises directing the electrode controller (optionally by a secondary controller) to direct the second positive electrode to transmit electrical current to the residual limb and the second negative electrode to receive the electrical current in response to the second symptom.

In some embodiments, the method comprises contacting a first sensor in response to the first symptom and contacting a second sensor in response to the second symptom over a period of time such as a course of at least 28 days, wherein the method is effective at reducing chronic symptoms of the phantom limb syndrome independent from treating acute symptoms by generating electrical current in the residual limb over the period of time. In some specific embodiments, reduction in chronic symptoms of the phantom limb syndrome is assessed with a Visual Analog Scale. Without limiting this specification or any patent claim that matures from this disclosure, repeated use of the systems of this disclosure reduces chronic symptoms of phantom limb syndrome, which can optionally be assessed with a Visual Analog Scale.

Treating an acute symptom refers to treating a symptom while a subject experiences the symptom, and acute efficacy refers to real-time efficacy at alleviating the acute symptom. Reducing chronic symptoms refers to reducing one or both of the frequency and severity of the symptom over time. Reducing chronic symptoms of the phantom limb syndrome independent from treating acute symptoms refers to reducing one or both of the frequency and severity of the symptom over time independent from treating an acute symptom; for example, after using a system described herein for a period of time (such as a course of at least 28 days), a subject may find that he or she experiences less frequent symptoms of phantom limb syndrome and that the symptoms are less severe independent from whether the subject actually treats any given symptom with the system.

Each amputee has a brain that comprises a somatosensory cortex. In some embodiments, the method is effective to activate different areas of the somatosensory cortex when different electrodes of the array of electrodes transmit and receive electrical current to and from the residual limb.

Without limiting this specification or any patent claim that matures from this disclosure, repeated use of the systems of this disclosure reduces chronic symptoms of phantom limb syndrome by neuromodulation in the somatosensory cortex.

The somatosensory cortex of the brain of an amputee typically includes a region for processing sensations of the missing body part. In some embodiments, the method comprises transmitting electrical current through the residual limb from electrodes of the array of electrodes periodically over a period of time such as a course of at least 28 days; and the method is effective to cause neuromodulation such that the electrical current causes activation in the region for processing sensations of the missing body part following the period of time. In some specific embodiments, the method comprises contacting one or more sensors and transmitting electrical current through the residual limb from a corresponding two or more electrodes periodically over the period of time; and the method is effective to cause neuromodulation such that the electrical current causes activation in the region for processing sensations of the missing body part following the period of time. In some very specific embodiments, the method comprises contacting the one or more sensors in response to a symptom of the phantom limb syndrome.

In some embodiments, the method comprises contacting two or more sensors to transmit electrical current through the residual limb from two or more different positive electrodes to two or more different negative electrodes periodically over a period of time such as a course of at least 28 days; and the method is effective to cause neuroplasticity-driven cortical remapping in the somatosensory cortex of the brain of the amputee following the period of time such that electrical current transmitted through the residual limb activates different areas of the somatosensory cortex after the period of time relative to before the period of time.

In some embodiments, each of the wires is in electrical communication with at least one electrode in an array of electrodes or in a pad.

In some embodiments, the liner is configured to receive the residual limb such that each electrode is in electrical communication with the residual limb.

In some embodiments, the interior surface of the substrate comprises an electrode aperture for each electrode of the array of electrodes or the pad such that each electrode aperture exposes a conductive surface of each electrode to contact the residual limb when it is in the liner.

In some embodiments, an array of electrodes is configured in the substrate such that each electrode of the array of electrodes is a paired electrode that can be paired with at least one other electrode of the array of electrodes, wherein, when the array of electrodes is in electrical communication with the residual limb, then each paired electrode can (1) transmit electrical current through the residual limb to a negative electrode of the array of electrodes with which the paired electrode is paired and/or (2) receive electrical current through the residual limb from a positive electrode of the array of electrodes with which the paired electrode is paired. In some specific embodiments, the array of electrodes is configured in the polymer liner such that each electrode of the array of electrodes is a paired electrode that can be paired with at least two other electrodes of the array of electrodes such that, when the array of electrodes is in electrical communication with the residual limb, then each paired electrode can (1) transmit electrical current through the residual limb both to a first negative electrode with which the paired electrode is paired and, independently, to a second negative electrode with which the paired electrode is paired and/or (2) receive electrical current through the residual limb from both a first positive electrode with which the paired electrode is paired and, independently, from a second positive electrode with which the paired electrode is paired.

In some embodiments, the electrode or array of electrodes is configured such that transmitting and receiving electrical current through the residual limb stimulates nerve fibers in the residual limb.

In some embodiments, the array of electrodes is configured such that when (1) two or more electrodes of the array of electrodes are activated and (2) the two or more electrodes are in electrical communication with the residual limb, then one activated electrode of the activated two or more electrodes transmits electrical current though the residual limb and another activated electrode of the activated two or more electrodes receives the electrical current that is transmitted through the residual limb.

In some embodiments, the liner is a product produced by a process in which (a) a substrate comprising the wires and the electrodes is placed in a mold and (b) liquid polymer is then poured into the mold such that the wires and the array of electrodes become embedded in the polymer thereby producing the liner. For example, the liner may be a polymer liner produced by pouring liquid polymer or monomers thereof into the mold.

In some embodiments, the liner is a polymer liner that comprises a polymer selected from silicone, polyurethane, and thermoplastic elastomer.

In some embodiments, the substrate is a polymer that comprises a polymer selected from silicone, polyurethane, and thermoplastic elastomer. Selecting a substrate polymer compatible with a liner polymer results in better fusion between the substrate and liner and avoid space delamination.

In some embodiments, the substrate is one or more substrates comprising the wires and the electrodes. For example, the substrate may be one substrate with 4-16 electrodes or two substrates with 2-8 electrodes each.

In some embodiments, each electrode of the array of electrodes is a stimulating electrode that is configured to transmit and/or receive electrical current that stimulates neurons in the residual limb when the stimulating electrode is in electrical communication with the residual limb. Suitable stimulating electrodes include, for example, carbon rubber electrodes.

In some embodiments, each electrode of the array of electrodes is configured to transmit, receive, or both transmit and receive pulsed electrical current that has an amplitude of at least 30 milliamps. In some specific embodiments, each electrode of the array of electrodes is configured to transmit, receive, or both transmit and receive pulsed electrical current that has a pulse frequency at least 20 and up to 180 pulses per second, a pulse width of up to 100 microseconds, and an amplitude of up to 100 milliamps.

In some embodiments, each electrode of the array of electrodes is a stimulating electrode that is configured to transmit and/or receive electrical current that stimulates Aβ nerve fibers in the residual limb when the stimulating electrode is in electrical communication with the residual limb.

In some embodiments, each electrode of the array of electrodes is configured to modulate the activation of myelinated Aδ nerve fibers and/or unmyelinated C nerve fibers in the residual limb.

In some embodiments, the array of electrodes comprises a ring of electrodes. The ring of electrodes consists of four or more electrodes of the array of electrodes that are each paired with exactly two other electrodes of the ring of electrodes. The ring of electrodes comprises a first electrode, a second electrode, a third electrode, and a fourth electrode, and the array of electrodes is configured to transmit electrical current through the residual limb between (1) the first electrode and the second electrode, between (2) the second electrode and the third electrode, and between (3) the third electrode and the fourth electrode. In some specific embodiments, the array of electrodes is configured to transmit electrical current through the residual limb between the fourth electrode and the first electrode. In some specific embodiments, the ring of electrodes encircles the inner surface of the liner such that the ring of electrodes encircles the void space or the residual limb within the void space.

In some embodiments, the array of electrodes comprises a second ring of electrodes; the second ring of electrodes consists of four or more electrodes of the array of electrodes that are each paired with exactly two other electrodes of the second ring of electrodes; the second ring of electrodes comprises the first electrode, the second electrode, a fifth electrode, and a sixth electrode; and the array of electrodes is configured to transmit electrical current through the residual limb between (4) the first electrode and the fifth electrode and between (5) the fifth electrode and the sixth electrode. In some specific embodiments, the array of electrodes is configured to transmit electrical current through the residual limb between (6) the sixth electrode and the second electrode.

In some embodiments, the array of electrodes comprises a third ring of electrodes; the third ring of electrodes consists of four or more electrodes of the array of electrodes that are each paired with exactly two other electrodes of the third ring of electrodes; the third ring of electrodes comprises the fifth electrode, the sixth electrode, a seventh electrode, and an eighth electrode; and the array of electrodes is configured to transmit electrical current through the residual limb between (7) the sixth electrode and the seventh electrode and between (8) the seventh electrode and the eighth electrode. In some specific embodiments, the array of electrodes is configured to transmit electrical current through the residual limb between (9) the eighth electrode and the fifth electrode.

In some embodiments, the array of electrodes comprises one, two, three, four, five, six, seven, or eight of an anterior-lateral-proximal electrode, a posterior-lateral-proximal electrode, an anterior-lateral-distal electrode, a posterior-lateral-distal electrode, an anterior-medial-proximal electrode, a posterior-medial-proximal electrode, an anterior-medial-distal electrode, and a posterior-medial-distal electrode.

Various aspects of this disclosure relate to a method of using the system described anywhere herein, comprising (a) providing a liner as described anywhere herein; (b) inserting the residual limb into the void space such that each electrode of the array of electrodes contacts the residual limb; and (c) transmitting electrical current through the residual limb between one, two, three, four, five, six, seven, eight, nine, ten, eleven, or twelve of (1) the anterior-lateral-proximal electrode and the posterior-lateral-proximal electrode; (2) the posterior-lateral-proximal electrode and the posterior-medial-proximal electrode; (3) the posterior-medial-proximal electrode and the anterior-medial-proximal electrode; (4) the anterior-medial-proximal electrode and the anterior-lateral-proximal electrode; (5) the anterior-lateral-distal electrode and the posterior-lateral-distal electrode; (6) the posterior-lateral-distal electrode and the posterior-medial-distal electrode; (7) the posterior-medial-distal electrode and the anterior-medial-distal electrode; (8) the anterior-medial-distal electrode and the anterior-lateral-distal electrode; (9) the anterior-lateral-proximal electrode and the anterior-lateral-distal electrode; (10) the posterior-lateral-proximal electrode and the posterior-lateral-distal electrode; (11) the posterior-medial-proximal electrode and the posterior-medial-distal electrode; and (12) the anterior-medial-proximal electrode and the anterior-medial-distal electrode.

Various aspects of this disclosure relate to a method of using the system described anywhere herein, comprising (a) providing a liner as described anywhere herein; (b) inserting the residual limb into the void space such that each electrode of the array of electrodes contacts the residual limb; (c) transmitting electrical current through the residual limb between a first two electrodes of the array of electrodes; (d) transmitting electrical current through the residual limb between a second two electrodes of the array of electrodes; (e) transmitting electrical current through the residual limb between a third two electrodes of the array of electrodes; and (f) transmitting electrical current through the residual limb between a fourth two electrodes of the array of electrodes. In some embodiments, the electrodes of the first two electrodes, the second two electrodes, the third two electrodes, and the fourth two electrodes are each independently selected from four, five, six, seven, or eight different electrodes of the array of electrodes such that the first two electrodes, the second two electrodes, the third two electrodes, and the fourth two electrodes each consist of a different two electrodes. In some specific embodiments, the first two electrodes consist of a first electrode and a second electrode; the second two electrodes consist of the second electrode and a third electrode; the third two electrodes consist of the third electrode and a fourth electrode; and the fourth two electrodes consist of the fourth electrode and the first electrode.

Various aspects of this disclosure relate to a system for modulating nerve activation in a residual limb of an amputee, comprising a polymer liner, wires that are at least partially embedded in the polymer liner, and an array of electrodes that are partially embedded in the liner, wherein: (1) the liner comprises silicone, polyurethane, or a thermoplastic elastomer; (2) the liner is a single, unified structure that consists of a tube comprising a wall, a closed end that is continuous with the wall, an edge that defines a terminus of the wall, a two-dimensional open end bounded by the edge, and a three-dimensional void space bounded by the closed end, the wall, and the open end; (3) the void space is configured to receive the residual limb through the open end; (4) the liner comprises a concave interior surface of the tube and a convex exterior surface of the tube, wherein the edge defines a boundary between the concave interior surface and the convex exterior surface; (5) the liner comprises one or more wire apertures that encircle the wires such that the wires exit the liner through the one or more wire apertures; (6) each wire of the wires is in electrical communication with at least one electrode of the array of electrodes; (7) the interior surface of the polymer liner comprises an electrode aperture for each electrode of the array of electrodes, such that each electrode aperture exposes a conductive surface of an electrode to either the void space or the residual limb within the void space; (8) the liner is configured to receive the residual limb such that each electrode of the array of electrodes is in electrical communication with the residual limb; (9) the array of electrodes is configured in the liner such that each electrode of the array of electrodes is a paired electrode that can be paired with at least one other electrode of the array of electrodes, wherein, when the array of electrodes is in electrical communication with the residual limb, then each paired electrode can (a) transmit electrical current through the residual limb to a negative electrode of the array of electrodes with which the paired electrode is paired and/or (b) receive electrical current through the residual limb from a positive electrode of the array of electrodes with which the paired electrode is paired; (10) the array of electrodes is configured such that transmitting and receiving electrical current through the residual limb stimulates nerve fibers in the residual limb; (11) the array of electrodes is configured such that when (a) two or more electrodes of the array of electrodes are activated and (b) the two or more electrodes are in electrical communication with the residual limb, then one activated electrode of the activated two or more electrodes transmits electrical current though the residual limb and another activated electrode of the activated two or more electrodes receives the electrical current that is transmitted through the residual limb; (12) each electrode of the array of electrodes is a stimulating electrode that is configured to transmit and/or receive electrical current that stimulates Aβ nerve fibers in the residual limb when the stimulating electrode is in electrical communication with the residual limb; (13) each electrode of the array of electrodes is configured to transmit, receive, or both transmit and receive pulsed electrical current that has an amplitude of at least 30 milliamps; and/or (14) the array of electrodes comprises at least one ring of electrodes, wherein a ring of electrodes consists of four or more electrodes of the array of electrodes that are each paired with exactly two other electrodes of the ring of electrodes.

Various aspects of this disclosure relate to a system for modulating nerve activation in a residual limb of an amputee, comprising a polymer liner, wires that are at least partially embedded in the polymer liner, and an array of electrodes that are partially embedded in the polymer liner, wherein: (1) the liner comprises silicone, polyurethane, or a thermoplastic elastomer; (2) the liner is non-conductive; (3) the liner is a single, unified structure that comprises a tube comprising a wall, a closed end that is continuous with the wall, an edge that defines a terminus of the wall, a two-dimensional open end bounded by the edge, and a three-dimensional void space bounded by the closed end, the wall, and the open end; (4) the void space is configured to receive the residual limb such that the residual limb exits the tube through the open end; (5) the polymer liner comprises a concave interior surface of the tube and a convex exterior surface of the tube, wherein the edge defines a boundary between the concave interior surface and the convex exterior surface; (6) the edge of the tube comprises one or more wire apertures that encircle the wires such that the wires exit the polymer liner through the edge; (7) the wires are at least partially embedded in the polymer liner because the wires exit the polymer liner through the edge; (8) the interior surface of the polymer liner comprises an electrode aperture for each electrode of the array of electrodes, such that each electrode aperture exposes a conductive surface of an electrode to either the void space or the residual limb within the void space; (9) the array of electrodes is partially embedded in the polymer liner because each electrode aperture exposes a conductive surface of an electrode to either the void space or the residual limb within the void space; (10) each electrode of the array of electrodes is medical-grade, carbon rubber electrode that is capable of conducting at least 30 milliamps of pulsed electrical current; (11) each electrode of the array of electrodes is in electrical communication with at least one of the wires; (12) the array of electrodes comprises at least eight electrodes; (13) four distal electrodes of the array of electrodes are positioned closer to the closed end than the open end of the tube; (14) four proximal electrodes of the array of electrodes are positioned between the four distal electrodes and the open end of the tube; (15) the polymer liner is configured to receive the residual limb such that each electrode of the array of electrodes is in electrical communication with the residual limb; (16) each electrode of the array of electrodes is a paired electrode that is paired with at least two other electrodes of the array of electrodes such that, when the array of electrodes is in electrical communication with the residual limb, then each paired electrode can (a) transmit electrical current through the residual limb to a negative electrode of the array of electrodes with which the paired electrode is paired and/or (b) receive electrical current through the residual limb from a positive electrode of the array of electrodes with which the paired electrode is paired; (17) the array of electrodes is configured such that transmitting and receiving electrical current through the residual limb stimulates Aβ nerve fibers in the residual limb; and/or (18) the polymer liner is a product produced by a process in which (a) a substrate comprising the wires and the array of electrodes is placed in a mold and (b) liquid polymer is then poured into the mold such that the wires and the array of electrodes become embedded in the polymer thereby producing the polymer liner.

Various aspects of this disclosure relate to a system for modulating nerve activation in a residual limb of an amputee, comprising a liner, wires that are at least partially embedded in the liner, and an array of electrodes that are partially embedded in the liner, wherein: (1) the liner is a tube comprising a wall, a closed end that is continuous with the wall, an edge that defines a terminus of the wall, a two-dimensional open end bounded by the edge, and a three-dimensional void space bounded by the closed end, the wall, and the open end; (2) the void space is configured to receive the residual limb such that the residual limb exits the tube through the open end; (3) the liner comprises a concave interior surface of the tube and a convex exterior surface of the tube, wherein the edge defines a boundary between the concave interior surface and the convex exterior surface; (4) the liner comprises one or more wire apertures for connecting the wires to an external controller; (5) the interior surface of the liner comprises an electrode aperture for each electrode of the array of electrodes, such that each electrode aperture exposes a conductive surface of an electrode to either the void space or the residual limb within the void space; (6) the array of electrodes is partially embedded in the polymer liner because each electrode aperture exposes a conductive surface of an electrode to either the void space or the residual limb within the void space; (7) each electrode of the array of electrodes is configured to conduct electrical current; (8) each electrode of the array of electrodes is in electrical communication with at least one wire; (9) the polymer liner is configured to receive the residual limb such that each electrode of the array of electrodes is in electrical communication with the residual limb; and (10) each electrode of the array of electrodes is a paired electrode that is paired with at least one other electrode of the array of electrodes such that, when the array of electrodes is in electrical communication with the residual limb, then each electrode can (a) transmit electrical current through the residual limb to a negative electrode with which the electrode is paired and/or (b) receive electrical current through the residual limb from a positive electrode with which the electrode is paired.

Various aspects of this disclosure relate to a system for modulating nerve activation in a residual limb of an amputee, comprising a liner that comprises an array of electrodes, wherein: (1) the liner comprises a tube comprising a wall, an edge that defines a terminus of the wall, a two-dimensional open end bounded by the edge, and a three-dimensional void space bounded by the wall; (2) the void space is configured to receive the residual limb such that each electrode of the array of electrodes is in electrical communication with the residual limb; (3) the liner comprises an electrode aperture for each electrode of the array of electrodes such that each electrode aperture exposes a conductive surface of each electrode to either the void space or the residual limb within the void space; (4) each electrode of the array of electrodes is paired with at least one other electrode of the array of electrodes such that, when the array of electrodes is in electrical communication with the residual limb, then each electrode can (a) transmit electrical current through the residual limb to a negative electrode with which the electrode is paired and/or (b) receive electrical current through the residual limb from a positive electrode with which the electrode is paired; and (5) the array of electrodes is configured such that transmitting and receiving electrical current through the residual limb stimulates nerve fibers in the residual limb.

Figure 10:
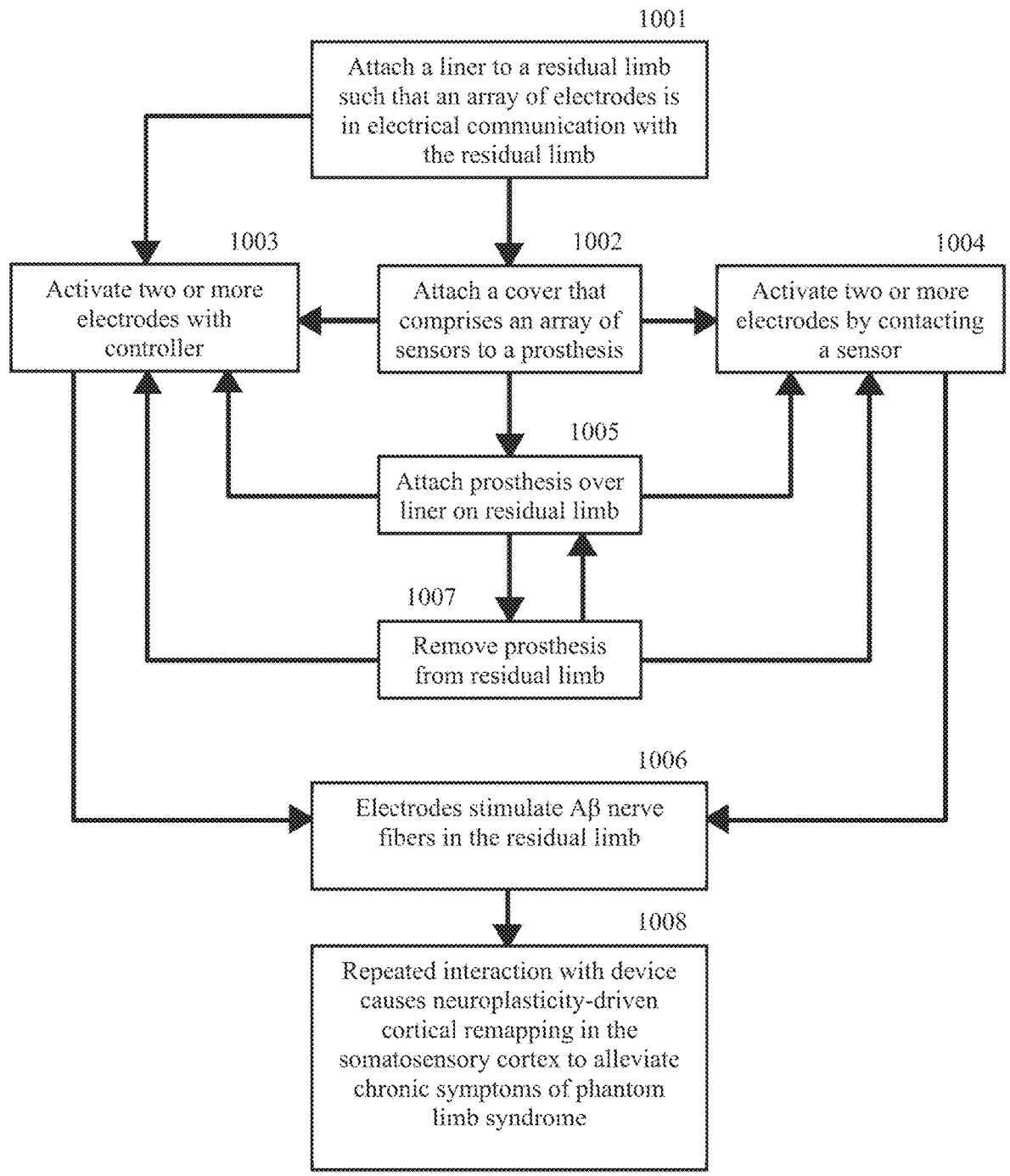
FIG. 10 is a flowchart illustrating methods that support that depicts use of the system.

FIG. 10 depicts a method of using a system as described herein. An amputee may either first attach a liner to his or her residual limb such that each electrode of the array of electrodes is in electrical communication with the residual limb 1001 or attach a cover to his or her prosthesis 1002. After the amputee attaches the liner to his or her residual limb 1001, the amputee can direct a controller to cause an electrode to transmit electrical current to the residual limb and another electrode to receive the electrical current from the residual limb 1003. The controller may be either an electrode controller or a secondary controller as described herein. After the cover is attached to the prosthesis 1002, contacting one or more sensors of an array of sensors of the cover will cause an electrode to transmit electrical current to the residual limb and another electrode to receive the electrical current from the residual limb 1004. Transmitting electrical current to the residual limb stimulates the Aβ nerve fibers in the residual limb 1006, which can treat one or more symptoms of phantom limb syndrome as described herein. The amputee can advantageously detach the prosthesis from the residual limb 1007 and nevertheless still direct the controller to transmit electrical current to the residual limb 1003 and also contact one or more sensors to transmit electrical current to the residual limb 1004, for example, to treat symptoms of phantom limb syndrome when the amputee is not wearing the prosthesis such as after the amputee has removed the prosthesis to sleep. Repeated use of the system over a period of time is generally effective at reducing chronic symptoms of phantom limb syndrome 1008, for example, as assessed with a Visual Analog Scale, independent from treating acute symptoms by generating electrical current in the residual limb. Without limiting this specification or any patent claim that matures from this disclosure, reduction in chronic symptoms of phantom limb syndrome 1008 are caused by neuroplasticity-driven cortical remapping in the somatosensory cortex of the brain, which can be assessed by scalp electroencephalography ("EEG").

In some embodiments, the method comprises simultaneously performing scalp EEG on the amputee and transmitting electrical current through the residual limb from a first positive electrode to a first negative electrode during the EEG to produce an electrogram.

In some embodiments, the method comprises simultaneously performing EEG on the amputee and transmitting electrical current through the residual limb from a positive electrode of the array of electrodes to a negative electrode of the array of electrodes during the EEG to produce an electrogram that depicts activation of the somatosensory cortex in response to the electrical current; and the system is configured such that the region for processing sensations of the missing body part displays activation in response to the electrical current in the electrogram. In some specific embodiments, simultaneously performing EEG on the amputee and transmitting the electrical current through the residual limb is performed a period of time, such as a course of at least 28 days, after an amputee first began using the system. In some very specific embodiments, the method comprises contacting one or more sensors of the array of sensors to transmit electrical current through the residual limb over a period of time such as a course of at least 28 days, wherein the EEG is performed following the period of time.

In some embodiments, the method comprises simultaneously performing EEG on the amputee and transmitting electrical current through the residual limb from a first positive electrode to a first negative electrode during the EEG to produce an electrogram that depicts activation of the somatosensory cortex in response to the electrical current; the method comprises simultaneously performing EEG on the amputee and transmitting electrical current through the residual limb during the EEG from a second positive electrode to a second negative electrode to produce an electrogram that depicts activation of the somatosensory cortex in response to the electrical current; and the system is configured such that the first positive electrode and the first negative electrode activate a first position in the somatosensory cortex, the second positive electrode and the second negative electrode activate a second position in the somatosensory cortex, and the electrogram depicts that electrical current transmitted through the residual limb by the first positive electrode to the first negative electrode activates different areas of the somatosensory cortex than electrical current transmitted through the residual limb by the second positive electrode to the second negative electrode. In some specific embodiments, the method comprises contacting a first sensor, which corresponds to the first positive electrode and the first negative electrode, to transmit electrical current through the residual limb periodically over a period of time such as a course of at least 28 days; and the method comprises contacting a second sensor, which corresponds to the second positive electrode and the second negative electrode, to transmit electrical current through the residual limb periodically over the period of time, wherein the EEG is performed following the period of time. Without limiting this specification or any patent claim that matures from this disclosure, neuromodulation in the somatosensory cortex by the systems of this disclosure may be detected with an EEG.

In some embodiments, the method comprises carrying out specific processes with at least one controller or electronic device, such as a computing device. In some embodiments, the method comprises performing a variety of programs for electrical current stimulation applications to a residual limb, including transcutaneous electrical nerve stimulation or electrical muscle stimulation treatment. The electronic devices may include any electronic devices known in the art, including wearable devices and user devices (e.g., smartphones, laptops, tablets, personal computers, desktop computing devices).

Other example user devices may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

The electronic devices associated with the user may include one or more of the following functionalities: 1) measuring physiological data, 2) storing measured data, 3) processing data, 4) providing outputs (e.g., via GUIs) to a user based on the processed data, and 5) communicating data with one another and/or other computing devices. Different electronic devices may perform one or more of the functionalities.

Some electronic devices may measure physiological parameters of a user, such as photoplethysmography waveforms, continuous skin temperature, a pulse waveform, respiration rate, heart rate, heart rate variability (HRV), actigraphy, galvanic skin response, pulse oximetry, blood oxygen saturation ($SpO_2$), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a mobile device application, or a server computing device may process received physiological data that was measured by other devices.

In some implementations, a user may operate, or may be associated with, multiple electronic devices, some of which may measure physiological parameters and some of which may process the measured physiological parameters. In some implementations, a user may have an electronic device that measures physiological parameters. The user may also have, or be associated with, a user device (e.g., mobile device, smartphone), where the electronic device and the user device are communicatively coupled to one another. In some cases, the user device may receive data from the electronic device and perform some/all of the calculations described herein. In some implementations, the user device may also measure physiological parameters described herein, such as motion/activity parameters.

Figure 11:
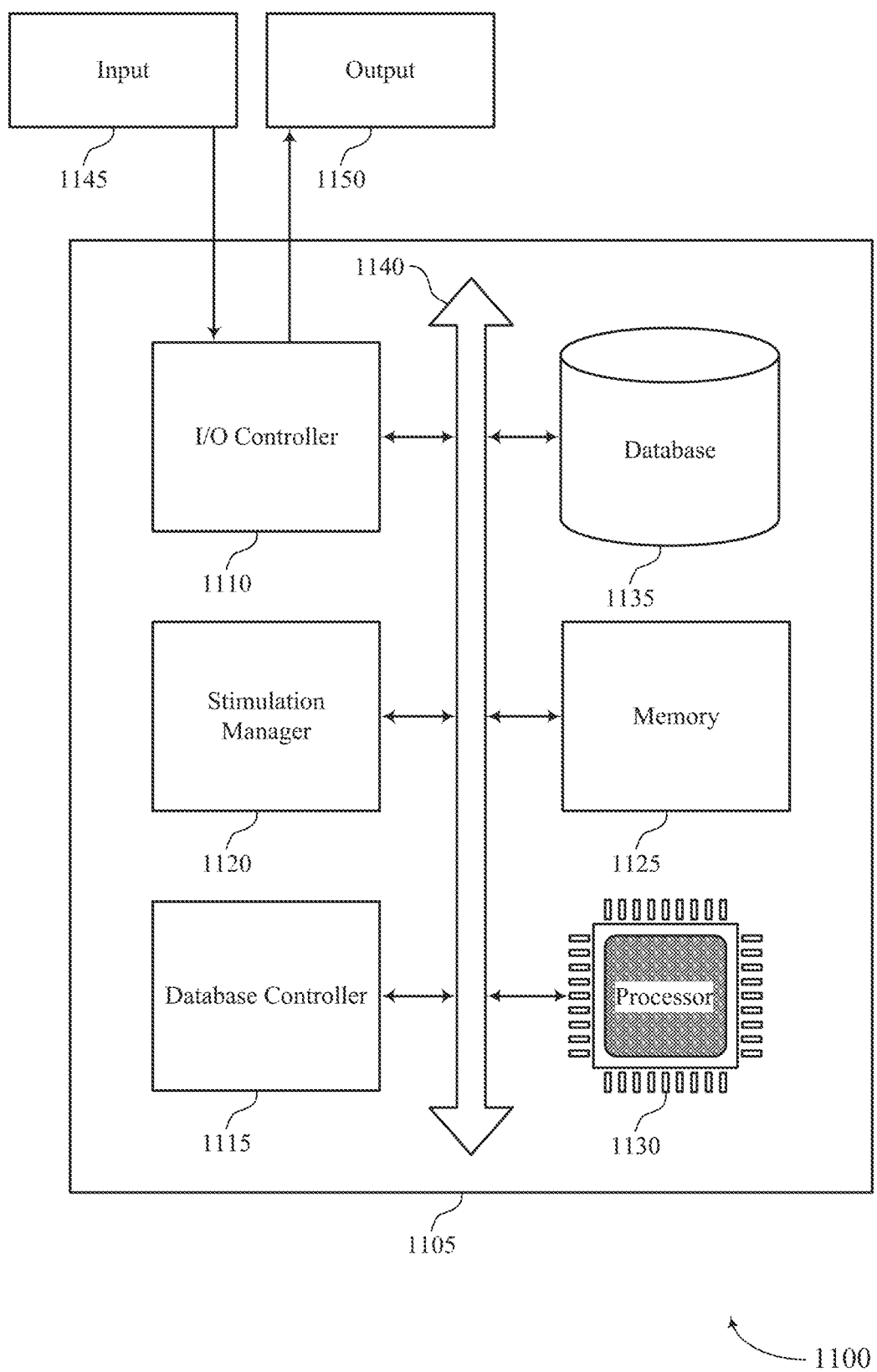
FIG. 11 depicts a device that supports residual limb electrical stimulation systems and methods in accordance with aspects of the present disclosure.

FIG. 11 shows a diagram of a system 1100 including a device 1105 that supports residual limb electrical stimulation systems and methods in accordance with aspects of the present disclosure. The device 1105 may be an example of or include components of the system as described herein. The device 1105 may include components for bi-directional data communications including components for transmitting and receiving communications, such as a matching manager 1120, an I/O controller, such as an I/O controller 1110, a database controller 1115, at least one memory 1125, at least one processor 1130, and a database 1135. These components may be in electronic communication or otherwise coupled (e.g., operatively, communicatively, functionally, electronically, electrically) via one or more buses (e.g., a bus 1140).

The I/O controller 1110 may manage input signals 1145 and output signals 1150 for the device 1105. The I/O controller 1110 may also manage peripherals not integrated into the device 1105. In some cases, the I/O controller 1110 may represent a physical connection or port to an external peripheral. In some cases, the I/O controller 1110 may utilize an operating system such as iOS®, ANDROID®, MS-DOS®, MS-WINDOWS®, OS/2®, UNIX®, LINUX®, or another known operating system. In other cases, the I/O controller 1110 may represent or interact with a modem, a keyboard, a mouse, a touchscreen, or a similar device. In some cases, the I/O controller 1110 may be implemented as part of a processor 1130. In some examples, a user may interact with the device 1105 via the I/O controller 1110 or via hardware components controlled by the I/O controller 1110.

The database controller 1115 may manage data storage and processing in a database 1135. In some cases, a user may interact with the database controller 1115. In other cases, the database controller 1115 may operate automatically without user interaction. The database 1135 may be an example of a single database, a distributed database, multiple distributed databases, a data store, a data lake, or an emergency backup database.

Memory 1125 may include random-access memory (RAM) and read-only memory (ROM). The memory 1125 may store computer-readable, computer-executable software including instructions that, when executed, cause at least one processor 1130 to perform various functions described herein. In some cases, the memory 1125 may contain, among other things, a basic I/O system (BIOS) which may control basic hardware or software operation such as the interaction with peripheral components or devices. The memory 1125 may be an example of a single memory or multiple memories. For example, the device 1105 may include one or more memories 1125.

The processor 1130 may include an intelligent hardware device (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some cases, the processor 1130 may be configured to operate a memory array using a memory controller. In other cases, a memory controller may be integrated into the processor 1130. The processor 1130 may be configured to execute computer-readable instructions stored in at least one memory 1125 to perform various functions (e.g., functions or tasks supporting stimulation systems and methods). The processor 1130 may be an example of a single processor or multiple processors. For example, the device 1105 may include one or more processors 1130.

The stimulation manager 1120 may support data processing in accordance with examples as disclosed herein. For example, the stimulation manager 1120 may be configured to support receiving, at a server and from a computing device associated with an electrode controller, a control pack or sensors, sensor feedback to electrical stimulation from the electrodes or biometric measurements. The stimulation manager 1120 may be configured to support generating stimulation program activity, results and measurements. The stimulation manager 1120 may be configured to support determining whether stimulation programs should be modified, repeated, or omitted. The stimulation manager 1120 may be configured to support communicating a result of determining whether stimulation programs should be modified, repeated, or omitted.

In some embodiments, the systems include modulating nerve activation in a residual limb of an amputee with a user interface configured to receive an input from the amputee and display an output; a processor, memory in electronic communication with the processor; and instructions stored in the memory and executable by the processor to cause the apparatus to: transmit, with an electrode controller in electrical communication with an electrode in a prosthetic liner substrate, electrical current through the residual limb; and stimulate Aβ nerve fibers in the residual limb responsive to transmitting electrical current with the electrode.

In some embodiments, the disclosed technology includes non-transitory computer-readable medium comprising instructions to cause a processor to: transmit with an electrode controller in electrical communication with an electrode in a prosthetic liner substrate, electrical current through a residual limb of an amputee; and stimulate Aβ nerve fibers in the residual limb responsive to transmitting electrical current with the electrode. The processor may be further configured to detect physiological parameters with at least one sensor; measures physiological data from the physiological parameters; store the measured physiological data; processes the measured physiological data; and provide outputs to a user or other computing device responsive to processing the measured physiological data.

It should be noted that the methods described above describe possible implementations, and that the operations and the steps may be rearranged, omitted, or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid space obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration)

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

As used herein, including in the claims, the article "a" before a noun is open-ended and understood to refer to "at least one" of those nouns or "one or more" of those nouns. Thus, the terms "a," "at least one," "one or more," "at least one of one or more" may be interchangeable. For example, if a claim recites "a component" that performs one or more functions, each of the individual functions may be performed by a single component or by any combination of multiple components. Thus, the term "a component" having characteristics or performing functions may refer to "at least one of one or more components" having a particular characteristic or performing a particular function. Subsequent reference to a component introduced with the article "a" using the terms "the" or "said" may refer to any or all of the one or more components. For example, a component introduced with the article "a" may be understood to mean "one or more components," and referring to "the component" subsequently in the claims may be understood to be equivalent to referring to "at least one of the one or more components." Similarly, subsequent reference to a component introduced as "one or more components" using the terms "the" or "said" may refer to any or all of the one or more components. For example, referring to "the one or more components" subsequently in the claims may be understood to be equivalent to referring to "at least one of the one or more components."

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

The following Exemplification describes a contemplated pilot clinical trial to illustrate certain aspects of this disclosure, and the Exemplification shall not be construed to limit this disclosure or any patent claim that matures from this disclosure.

EXEMPLIFICATION

A pilot clinical trial demonstrates that transcutaneous electrical stimulation of a residual limb in response to touching a prosthesis reduces symptoms of phantom limb syndrome.

A group of 15 amputee subjects who experience symptoms of phantom limb syndrome as a result of limb amputation are enrolled in a pilot clinical trial. Each subject has an intact limb that corresponds to the amputated limb. The subjects rate their level of pain associated with phantom limb syndrome using a Visual Analog Scale.

A system as described in the detailed description is provided to each subject. Briefly, the system comprises a prosthetic cover comprising an array of sensors, which control the activation of an array of electrodes in a liner that fits over the residual limb of an amputee.

Each subject is fitted with a liner, such that each electrode of the array of electrodes is in electrical communication with the residual limb. Each subject has an existing prosthetic, which is fitted with a cover comprising an array of sensors.

Each subject is fitted with EEG electrodes. Various regions of the intact limb are contacted by a researcher, and an electrogram is recorded for the intact limb. Then, while each subject is wearing his or her existing prosthetic, various regions of the cover of the prosthetic are contacted by the researcher to drive electrical current through the residual limb, and an electrogram is recorded for the prosthetic cover. The subject is instructed to watch as the intact limb and cover are contacted. The various regions of the intact limb and cover that are contacted correspond to each other both spatially and temporally.

Each subject is then instructed to apply pressure to his or her intact limb in a similar spatial and temporal pattern as the researcher while focusing his or her gaze on the areas of applied pressure, and an electrogram is recorded. Each subject is then instructed to apply pressure to his or her prosthetic cover in a similar spatial and temporal pattern as the researcher while focusing his or her gaze on the areas of applied pressure, and an electrogram is recorded.

Each subject is then instructed to take the system home. Each subject is given written instructions to apply pressure to the intact limb and prosthetic cover daily in the spatial and temporal pattern and to otherwise apply pressure to the prosthetic cover in response to symptoms of phantom limb syndrome as well as upon demand. Use of the system is recorded by the system in its computer memory. Each subject is also instructed to rate his or her level of pain associated with phantom limb syndrome on the Visual Analog Scale daily both before and after performing the written instructions.

After four weeks, each subject returns for a follow-up EEG, which is performed with substantially the same spatial and temporal contact pattern for the intact limb and prosthetic cover as administered for the initial EEG described above. The initial and follow-up electrograms are approximately the same for each intact limb. The initial and follow-up electrograms are significantly different for each amputated limb. For subjects with leg amputations, differences are greater for gamma waves detected near the medial region of the somatosensory cortex. The magnitude of difference between initial and follow-up EEGs correlates with frequency of system use as recorded by the system. These results indicate that the intervention results in neuroplasticity-driven cortical remapping in the subjects.

Following four weeks of the intervention, all subjects report lower levels of phantom limb pain on the Visual Analog Scale relative to before the intervention, which indicates long-term efficacy of the intervention. The magnitude in reduction of pain as reported on the Visual Analog Scale correlates with frequency of system use as recorded by the system. Following four weeks of the intervention, all subjects report lower levels of phantom limb pain on the Visual Analog Scale following performance of the spatial and temporal pattern intervention relative to immediately prior to the intervention, which indicates acute efficacy of the intervention.

The invention claimed is:

1. A method of modulating nerve activation in a residual limb of an amputee, comprising:
    providing a system that comprises:
        1) a prosthetic liner with a first polymer; and
        2) a substrate with a second polymer comprising a plurality of embedded electrodes and an embedded conductor,
        wherein the prosthetic liner is bonded to an outer surface of the substrate,
        wherein an inner surface of the substrate directly contacts the residual limb; and
        wherein the first polymer and the second polymer are polymer compatible;
    receiving the residual limb in the prosthetic liner and the substrate such that each electrode in the substrate is in contact with and in electrical communication with the residual limb;
    transmitting, with an electrode controller in electrical communication with each electrode, pulsed electrical current with a pulse frequency at least 20 and up to 180 pulses per second, a pulse width of up to 100 microseconds, and an amplitude of up to 100 milliamps, through the residual limb; and
    stimulating nerve fibers in the residual limb responsive to transmitting electrical current with the plurality of electrodes.

2. The method of claim 1, further comprising:
    stimulating muscles in the residual limb responsive to transmitting electrical current with the plurality of electrodes.

3. The method of claim 1, wherein the amputee presents with phantom limb syndrome; and further comprising treating one or more symptoms of the phantom limb syndrome with transmission of the electrical current.

4. The method of claim 1, further comprising:
    transmitting, with a secondary controller in wireless communication with the electrode controller, electrical current to the residual limb.

5. The method of claim 1, further comprising:
    receiving input, with a user interface, from the amputee;
    displaying an output based on the received input; and
    causing, with instructions stored in memory in electronic communication with a processor and executable by the processor, the apparatus to:
        transmit, with an electrode controller in electrical communication with an electrode in the substrate, electrical current through the residual limb; and
        stimulate nerve fibers in the residual limb responsive to transmitting electrical current with the electrode.

6. The method of claim 1, wherein the plurality of electrodes have an electrode three-dimensional configuration relative to the liner and to the substrate.

7. The method of claim 1, wherein the plurality of electrodes are configured in a ring that includes an anterior-lateral-proximal electrode, a posterior-lateral-proximal electrode, a posterior-medial-proximal electrode, and an anterior-medial-proximal electrode to encircle the residual limb.

8. The method of claim 1, wherein an interior surface of the substrate comprises an electrode aperture for each electrode or a pad such that each electrode aperture exposes a conductive surface of each electrode to contact the residual limb.

9. The method of claim 1,
    causing one or more electrodes to transmit electrical current to the residual limb with a secondary controller in wireless communication with the electrode controller.

10. The method of claim 9, wherein:
    the secondary controller is a computing device;
    the secondary controller is in wireless communication with the electrode controller; and
    the wireless communication is mediated by one or both of a Bluetooth or Wi-Fi connection between the mobile computing device and the plurality of electrodes.

11. The method of claim 1, wherein the liner comprises a polymer selected from silicone, polyurethane, and thermoplastic elastomer.

12. The method of claim 1, wherein the prosthetic liner is molded onto the outer surface of the substrate.

13. The method of claim 1, further comprising:
    modulating the activation of myelinated Aδ nerve fibers in the residual limb.

14. The method of claim 1, further comprising:
    transmitting electrical current through the residual limb between a first two electrodes in an array of electrodes;
    transmitting electrical current through the residual limb between a second two electrodes in the array of electrodes;
    transmitting electrical current through the residual limb between a third two electrodes in the array of electrodes; and
    transmitting electrical current through the residual limb between a fourth two electrodes in the array of electrodes.

15. The method of claim 1, further comprising:
    directing the electrode controller to direct a first positive electrode to transmit electrical current to the residual limb and a negative electrode to receive the electrical current in response to a first symptom.

16. The method of claim 15, further comprising:
directing the electrode controller to direct a second positive electrode to transmit electrical current to the residual limb and a second negative electrode to receive the electrical current in response to a second symptom.

17. The method of claim 1, further comprising:
directing a secondary controller to direct a first positive electrode to transmit electrical current to the residual limb and a first negative electrode to receive the electrical current in response to a first symptom.

18. The method of claim 17, further comprising:
directing a secondary controller to direct a second positive electrode to transmit electrical current to the residual limb and the second negative electrode to receive the electrical current in response to the second symptom.

19. The method of claim 17, further comprising:
simultaneously performing scalp electroencephalography on the amputee and transmitting electrical current through the residual limb during the electroencephalography to produce an electrogram.

20. The method of claim 1, wherein the first polymer and the second polymer are the same polymer.

21. The method of claim 1, wherein the first polymer and the second polymer are different polymers.

22. The method of claim 1, wherein the embedded conductor is a plurality of conductive wires.

23. The method of claim 1, wherein the electronic controller controls which electrode in an array of electrodes transmits electrical current through a specific region of the residual limb.

24. The method of claim 1, wherein each electrode in the substrate is in direct contact with the surface of the residual limb.

25. The method of claim 1, further comprising:
applying a conductive gel between the plurality of embedded electrodes and the residual limb to facilitate electrical communication between the plurality of embedded electrodes and the residual limb.

* * * * *